US011696744B2

(12) United States Patent
Park et al.

(10) Patent No.: US 11,696,744 B2
(45) Date of Patent: Jul. 11, 2023

(54) ULTRASOUND IMAGING APPARATUS FOR REGISTERING ULTRASOUND IMAGE WITH IMAGE FROM ANOTHER MODALITY AND METHOD OF OPERATING ULTRASOUND IMAGING APPARATUS

(71) Applicant: SAMSUNG MEDISON CO., LTD., Hongcheon-gun (KR)

(72) Inventors: Junsung Park, Seongnam-si (KR); Yuri Son, Seongnam-si (KR); Yeongseon Kim, Seongnam-si (KR); Jonghyon Yi, Seongnam-si (KR); Yeonmo Jeong, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 511 days.

(21) Appl. No.: 16/791,426

(22) Filed: Feb. 14, 2020

(65) Prior Publication Data
US 2020/0268348 A1 Aug. 27, 2020

(30) Foreign Application Priority Data

Feb. 26, 2019 (KR) ........................ 10-2019-0022580

(51) Int. Cl.
*A61B 8/00* (2006.01)
*A61B 8/08* (2006.01)
(Continued)

(52) U.S. Cl.
CPC ............ *A61B 8/463* (2013.01); *A61B 6/5217* (2013.01); *A61B 8/4245* (2013.01); *A61B 8/46* (2013.01);
(Continued)

(58) Field of Classification Search
CPC ... A61B 8/46–469; A61B 8/52; A61B 8/5207; A61B 8/5215; A61B 8/5238;
(Continued)

(56) References Cited

U.S. PATENT DOCUMENTS 8,731,264 B2   5/2014  Kruecker et al.
9,147,098 B2   9/2015  Iizuka et al.
(Continued)

FOREIGN PATENT DOCUMENTS

JP   4612057 B2   1/2011
JP   5361194 B2   12/2013
(Continued)

OTHER PUBLICATIONS

Anwar, Syed Muhammad, et al. "Medical image analysis using convolutional neural networks: a review." Journal of medical systems 42.11 (2018): 1-13.*
(Continued)

*Primary Examiner* — Carolyn A Pehlke
(74) *Attorney, Agent, or Firm* — Sughrue Mion, PLLC

(57) ABSTRACT

Provided are an ultrasound imaging apparatus and an operation method for registering an ultrasound image and an image from another modality. The ultrasound imaging apparatus may register the ultrasound image and the image from the other modality based on a three-dimensional positional relationship between at least one external electromagnetic sensor attached to a patient's body and an ultrasound probe and on a position of a feature point extracted from the image from the other modality.

21 Claims, 17 Drawing Sheets

(51) Int. Cl.
  *G06T 7/00* (2017.01)
  *G06T 7/33* (2017.01)
  *A61B 6/00* (2006.01)
  *G01R 33/48* (2006.01)

(52) U.S. Cl.
  CPC .......... *A61B 8/5261* (2013.01); *G06T 7/0012* (2013.01); *G06T 7/33* (2017.01); *A61B 6/5247* (2013.01); *A61B 8/4405* (2013.01); *A61B 8/464* (2013.01); *A61B 8/469* (2013.01); *A61B 8/5223* (2013.01); *G01R 33/4814* (2013.01); *G06T 2207/10072* (2013.01); *G06T 2207/10081* (2013.01); *G06T 2207/10088* (2013.01); *G06T 2207/10132* (2013.01); *G06T 2207/20084* (2013.01); *G06T 2207/30004* (2013.01)

(58) Field of Classification Search
  CPC ... A61B 8/5261; A61B 6/5247; A61B 6/5229; A61B 6/5211; A61B 6/52; A61B 6/46–469; G01R 33/4814
  See application file for complete search history.

(56) References Cited

U.S. PATENT DOCUMENTS

| | | | |
|---|---|---|---|
| 9,155,470 B2 | 10/2015 | Grbic et al. | |
| 9,504,436 B2 | 11/2016 | Suri et al. | |
| 9,949,723 B2 | 4/2018 | Oh et al. | |
| 2001/0036302 A1* | 11/2001 | Miller | G06T 7/33 |
| | | | 382/128 |
| 2006/0030768 A1 | 2/2006 | Ramamurthy et al. | |
| 2008/0009724 A1 | 1/2008 | Lee et al. | |
| 2008/0107312 A1* | 5/2008 | Von Berg | G06T 7/30 |
| | | | 382/128 |
| 2009/0054772 A1 | 2/2009 | Lin et al. | |
| 2010/0067768 A1 | 3/2010 | Ionasec et al. | |
| 2010/0298705 A1* | 11/2010 | Pelissier | A61B 8/4254 |
| | | | 600/443 |
| 2013/0237811 A1 | 9/2013 | Mihailescu et al. | |
| 2014/0193053 A1 | 7/2014 | Kadoury et al. | |
| 2015/0112196 A1* | 4/2015 | Tanaka | A61B 8/463 |
| | | | 600/437 |
| 2018/0092628 A1* | 4/2018 | Mine | A61B 8/483 |
| 2019/0000318 A1* | 1/2019 | Caluser | A61B 5/0073 |
| 2020/0323512 A1* | 10/2020 | Ng | A61B 8/467 |

FOREIGN PATENT DOCUMENTS

| | | |
|---|---|---|
| KR | 10-2007-0110965 A | 11/2007 |
| KR | 10-2016-0076868 A | 7/2016 |
| WO | 01/06924 A1 | 2/2001 |
| WO | 2017/202795 A1 | 11/2017 |

OTHER PUBLICATIONS

Communication dated Jul. 23, 2020, from the European Patent Office in counterpart European Application No. 20155209.8.
Xiaozhao Chen et al. "A review of Surgery Navigation System Based on Ultrasound Guidance" Proceedings of the IEEE, Jun. 2012 (5 pages total).
Minglei Yang et al. "Subject-specific real-time respiratory liver motion compensation method for ultrasound-MRI/CT fusion imaging" International Journal of Computer Assisted Radiology and Surgery, vol. 10, No. 5, Jun. 14, 2014, (13 pages).
Communication dated Feb. 15, 2023 by the European Patent Office in counterpart European Patent Application No. 20155209.8.

\* cited by examiner

FIG. 5
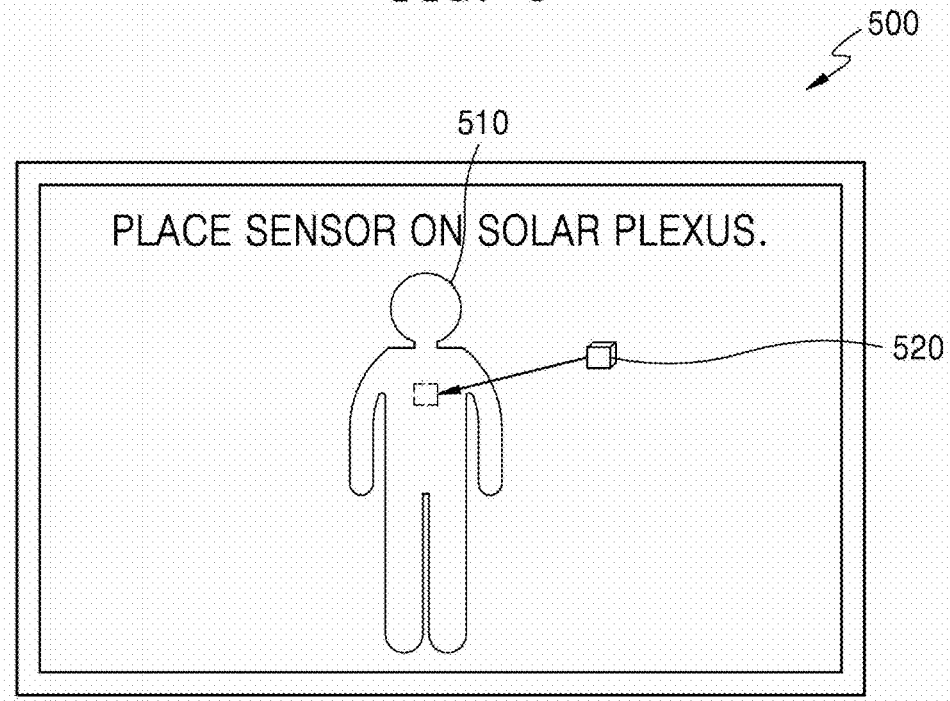
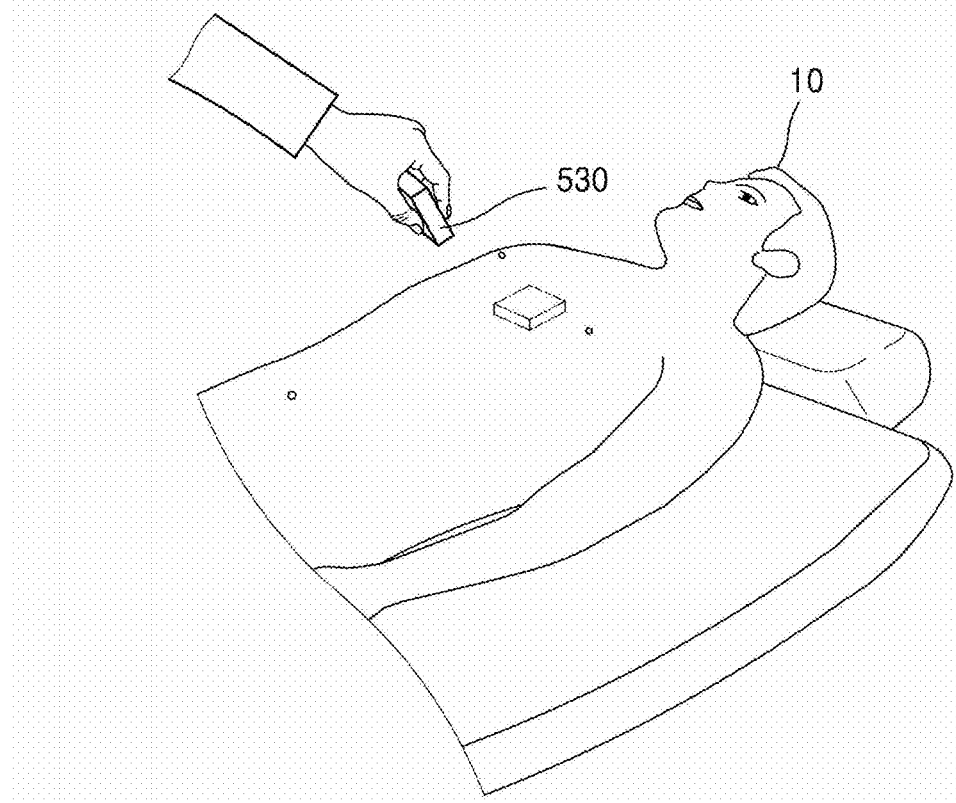

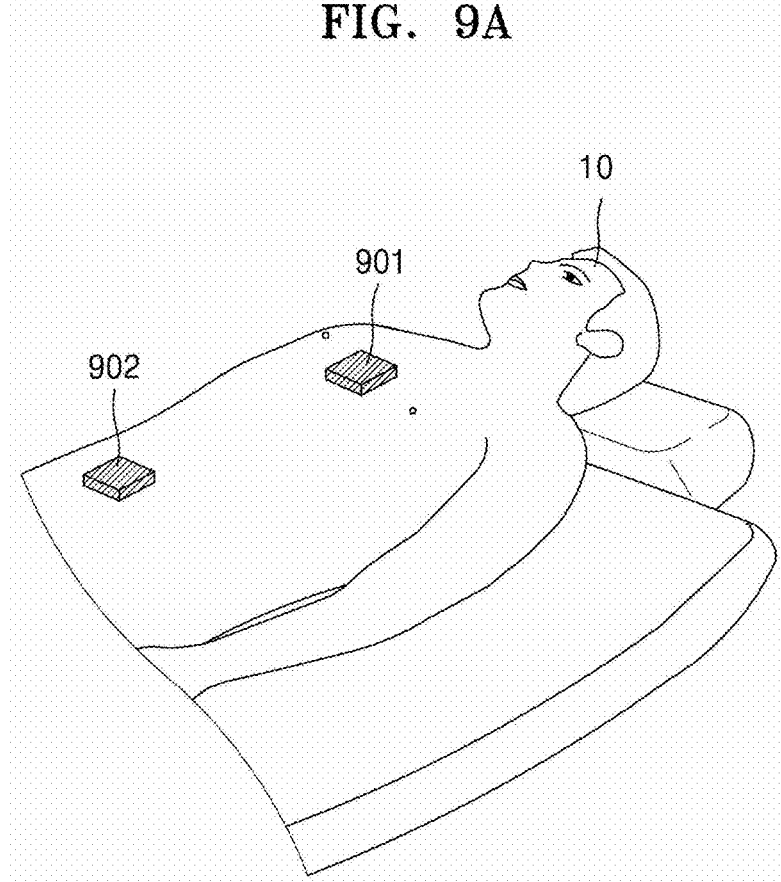

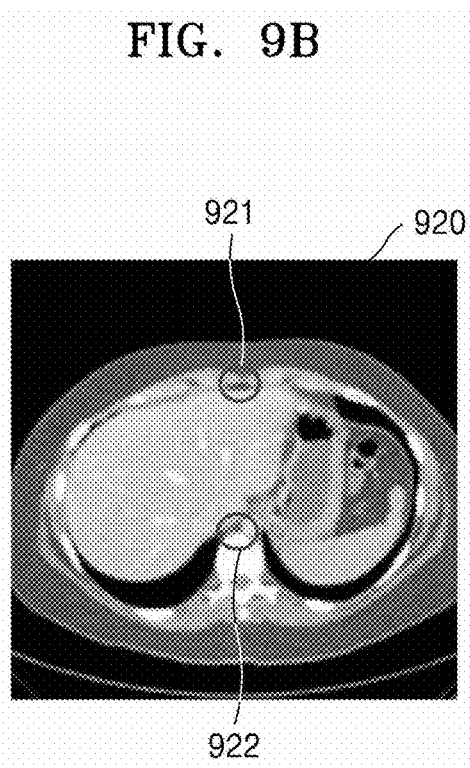

ULTRASOUND IMAGING APPARATUS FOR REGISTERING ULTRASOUND IMAGE WITH IMAGE FROM ANOTHER MODALITY AND METHOD OF OPERATING ULTRASOUND IMAGING APPARATUS

CROSS-REFERENCE TO RELATED APPLICATION

This application is based on and claims priority under 35 U.S.C. § 119 to Korean Patent Application No. 10-2019-0022580, filed on Feb. 26, 2019, in the Korean Intellectual Property Office, the disclosure of which is incorporated by reference herein in its entirety.

BACKGROUND

1. Field

The disclosure relates to an ultrasound imaging apparatus for registering an ultrasound image with an image from another modality and a method of operating the ultrasound imaging apparatus.

2. Description of Related Art

Ultrasound imaging apparatuses transmit ultrasound signals generated by transducers of a probe to an object and receive information about signals reflected from the object, thereby obtaining at least one ultrasound image of an internal part of the object (e.g., soft tissue or blood flow).

Ultrasound imaging apparatuses may register a real-time ultrasound image of an object with an image of the same object pre-acquired from another modality, such as a magnetic resonance (MR) image or a computed tomography (CT) image, and synthesize the registered ultrasound image and the image from the other modality and display the resulting synthesized image. According to a registration method of the related art, an ultrasound imaging apparatus uses at least one electromagnetic (EM) sensor attached to an ultrasound probe to detect a position and an orientation of the ultrasound probe, and registers an ultrasound image with an image from another modality by using information about the position and orientation of the ultrasound probe acquired via the EM sensor. However, the registration method of the related art requires user intervention for registration between the ultrasound image and the image from the other modality. Thus, the registration method requires a high level of user expertise and results in relatively low registration accuracy.

SUMMARY

Provided are ultrasound imaging apparatuses and operation methods for acquiring information about a position and an orientation of an ultrasound probe via an external electromagnetic (EM) sensor attached to a body part of a patient and registering an ultrasound image and an image from another modality based on the acquired information about the position and orientation.

Additional aspects will be set forth in part in the description which follows and, in part, will be apparent from the description, or may be learned by practice of the presented embodiments of the disclosure.

In accordance with an aspect of the disclosure, a method of registering a first image that is an ultrasound image and a second image that is an image from another modality includes: loading the second image pre-acquired for a patient; acquiring information about a position and an orientation of an ultrasound probe based on a three-dimensional (3D) positional relationship between at least one external EM sensor attached to a first feature point of a patient's body and an EM sensor of the ultrasound probe; extracting, from the second image, a second feature point corresponding to the first feature point; and registering the first and second images based on the 3D positional relationship between the at least one external EM sensor and the EM sensor of the ultrasound probe and a position of the second feature point extracted from the second image.

The registering of the first and second images may include: setting, as a reference point, a position of the at least one external EM sensor attached to the first feature point; and matching a position and an angle of the second image to those of the first image based on information about a distance and an angle between the reference point and the EM sensor of the ultrasound probe.

The extracting of the second feature point may include extracting the second feature point including characteristics of a body structure corresponding to the first feature point by applying an image processing algorithm to the second image.

The extracting of the second feature point may include extracting the second feature point based on at least one of a specific part of an object in the second image, an anatomical structure of the object in the second image, a resolution of the second image, and characteristics of the second image.

The extracting of the second feature point may include extracting the second feature point from the second image by using a deep neural network (DNN) including at least one of a convolution neural network (CNN) and a recurrent neural network (RNN), or by using a machine learning model including a support vector machine (SVM).

The extracting of the second feature point may include: receiving a user input for selecting, from the second image, a position of a structural feature point of the patient's body; and determining the position of the second feature point based on the received user input.

The method may further include correcting a registration error generated due to a difference of the position and an angle between the second feature point extracted from the second image and the at least one external EM sensor attached to a surface of the patient's body.

The correcting of the registration error may include: calculating a minimum distance between the second feature point extracted from the second image and a surface of the patient's body represented in the second image; and correcting a position error in the second image based on the calculated minimum distance.

The correcting of the registration error may include: calculating a relationship of a distance and an angle between the second feature point extracted from the second image and a surface of the patient's body represented in the second image; and correcting the position and angle of the second feature point based on the calculated relationship of the distance and angle.

The correcting of the registration error may include: acquiring information about an angle between first and second external EM sensors respectively attached onto structural feature points of the patient's body; and correcting an angular error in the second image based on the information about the angle between the first and second external EM sensors.

The method may further include displaying the first image in a first region of a display and the second image registered with the first image in a second region of the display.

The method may further include displaying, in the first image, a first marker indicating a position of the first feature point of the patient's body in the first image and displaying, in the second image, a second marker indicating the position of the second feature point extracted from the second image.

The method may further include displaying a graphical user interface (GUI) indicating a signal strength of each of the at least one external EM sensor.

In accordance with another aspect of the disclosure, an ultrasound imaging apparatus for registering a first image that is an ultrasound image and a second image that is an image from another modality includes: an ultrasound probe including an EM sensor; a storage storing the second image pre-acquired for a patient; a memory storing at least one instruction for controlling an operation of the ultrasound imaging apparatus; and a processor configured to execute the at least one instruction stored in the memory to: load the second image from the storage; acquire information about a position and an orientation of the ultrasound probe based on a 3D positional relationship between at least one external EM sensor attached to a first feature point of a patient's body and the EM sensor of the ultrasound probe; extract, from the second image, a second feature point corresponding to the first feature point; and register the first and second images based on the 3D positional relationship between the at least one external EM sensor and the EM sensor of the ultrasound probe and on a position of the second feature point extracted from the second image.

The processor may be further configured to execute the at least one instruction to: set, as a reference point, a position of the at least one external EM sensor attached to the first feature point; and match a position and an angle of the second image to those of the first image based on information about a distance and an angle between the reference point and the EM sensor of the ultrasound probe.

The processor may be further configured to execute the at least one instruction to extract the second feature point including characteristics of a body structure corresponding to the first feature point by applying an image processing algorithm to the second image.

The processor may be further configured to execute the at least one instruction to extract the second feature point based on at least one of a specific part of an object in the second image, an anatomical structure of the object in the second image, a resolution of the second image, and characteristics of the second image.

The processor may be further configured to execute the at least one instruction to extract the second feature point from the second image by using a DNN including at least one of a CNN and a RNN, or by using a machine learning model including a SVM.

The ultrasound imaging apparatus may include: a user input interface configured to receive a user input for selecting, from the second image, a position of a structural feature point of the patient's body, wherein the processor is further configured to execute the at least one instruction to determine the position of the second feature point based on the received user input.

The processor may be further configured to execute the at least one instruction to correct a registration error generated due to a difference of the position and an angle between the second feature point extracted from the second image and the at least one external EM sensor attached to a surface of the patient's body.

The processor may be further configured to execute the at least one instruction to: calculate a minimum distance between the second feature point extracted from the second image and a surface of the patient's body represented in the second image; and correct a position error in the second image based on the calculated minimum distance.

The processor may be further configured to execute the at least one instruction to: calculate a relationship of a distance and an angle between the second feature point extracted from the second image and a surface of the patient's body represented in the second image; and correct the position and angle of the second feature point based on the calculated relationship of the distance and angle.

The processor may be further configured to execute the at least one instruction to: acquire information about an angle between first and second external EM sensors respectively attached onto structural feature points of the patient's body; and correct an angular error in the second image based on the information about the angle between the first and second external EM sensors.

The ultrasound imaging apparatus may further include a display displaying the first image in a first region thereof and the second image registered with the first image in a second region thereof.

The display may further display, in the first image, a first marker indicating a position of the first feature point of the patient's body in the first image and display, in the second image, a second marker indicating the position of the second feature point extracted from the second image.

The display may further display a GUI indicating a signal strength of each of the at least one external EM sensor.

In accordance with another aspect of the disclosure, a computer program product includes a computer-readable storage medium including instructions to: load the second image pre-acquired for a patient; acquire information about a position and an orientation of an ultrasound probe based on a 3D positional relationship between at least one external EM sensor attached to a first feature point of a patient's body and an EM sensor of the ultrasound probe; extract, from the second image, a second feature point corresponding to the first feature point; and register the first and second images based on the 3D positional relationship between the at least one external EM sensor and the EM sensor of the ultrasound probe and on a position of the second feature point extracted from the second image.

BRIEF DESCRIPTION OF THE DRAWINGS

The above and other aspects, features, and advantages of certain embodiments of the disclosure will be more apparent from the following description taken in conjunction with the accompanying drawings in which reference numerals denote structural elements:

FIG. 5 illustrates an example of a user interface (UI) via which an ultrasound imaging apparatus instructs a user to attach an external electromagnetic (EM) sensor to a specific body part of a patient, according to an embodiment of the disclosure;

FIG. 9A illustrates external EM sensors attached onto a patient's body; FIG. 9B illustrates an example in which an ultrasound imaging apparatus extracts a feature point from an image from another modality, according to an embodiment of the disclosure.

DETAILED DESCRIPTION

Figure 1:
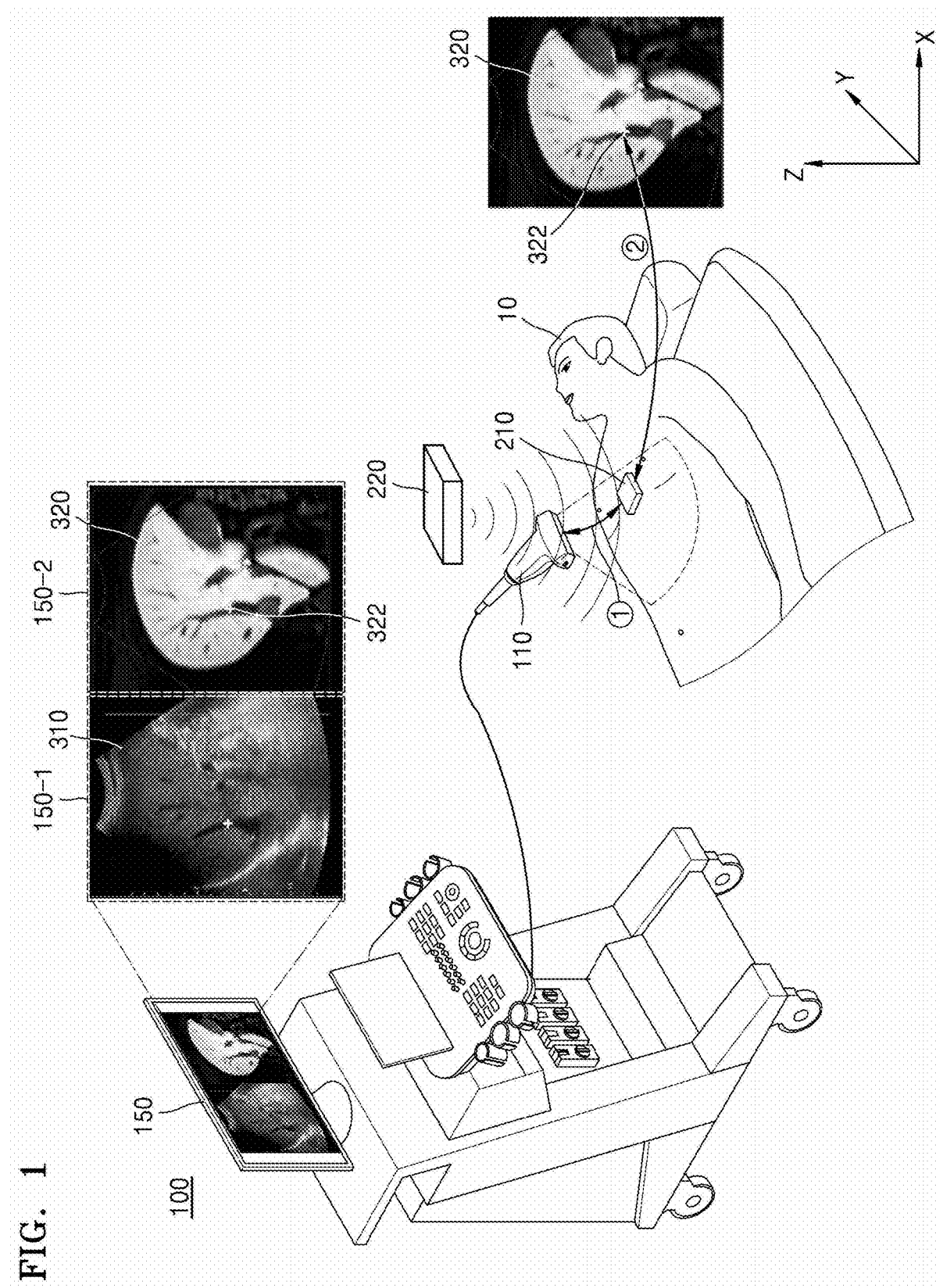
FIG. 1 illustrates an example in which an ultrasound imaging apparatus registers an ultrasound image and an image from another modality, according to an embodiment of the disclosure.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

As used herein, the term "and/or" includes any and all combinations of one or more of the associated listed items.

Expressions such as "at least one of," when preceding a list of elements, modify the entire list of elements and do not modify the individual elements of the list.

In the specification, an 'ultrasound image' refers to an image of an object processed based on ultrasound signals transmitted to the object and reflected therefrom.

Throughout the specification, 'an image from another modality" or "an image from a different modality" may include an image from a modality other than an ultrasound image, such as a medical image obtained by a medical imaging apparatus like a magnetic resonance imaging (MRI) apparatus, a computed tomography (CT) apparatus, or an X-ray imaging apparatus. For example, an image from another modality may refer to one of an MR image, a CT image, and X-ray image.

Also, in the present specification, an "object", which is a thing to be imaged, may include a human, an animal, or a part thereof. For example, an object may include a part of a human, that is, an organ or a tissue, or a phantom.

In the specification, a "feature point" may refer to a characteristic part of a human body exposed to the outside, such as a solar plexus, a navel, nipples, etc.

Throughout the specification, a "user" may be, but is not limited to, a medical expert, such as a medical doctor, a nurse, a medical laboratory technologist or a medical imaging expert, or a technician who repairs a medical apparatus.

FIG. 1 illustrates an example in which an ultrasound imaging apparatus 100 registers an ultrasound image and an image from another modality, according to an embodiment of the disclosure.

Referring to FIG. 1, the ultrasound imaging apparatus 100 may register a pre-acquired image 320 from another modality and an ultrasound image 310 obtained in real-time for a patient 10 and display the ultrasound image 310 and the pre-acquired image 320 from the other modality together on a display 150. In this case, the pre-acquired image 320 from the other modality refers to an image from a different modality, which is not the ultrasound image 310, such as one of an MR image, a CT image, and an X-ray image. However, the pre-acquired image 320 from the other modality is not limited to the examples listed above.

The ultrasound imaging apparatus 100 may acquire information about a position and an orientation of an ultrasound probe (hereinafter, referred to as 'position and orientation information of an ultrasound probe') 110, based on a three-dimensional (3D) positional relationship ① between at least one external electromagnetic (EM) sensor 210 attached to a feature point on a body of the patient 10 and an EM sensor included in the ultrasound probe 110. The at least one external EM sensor 210 may be attached by a user to a specific point representing characteristics of a body structure of the patient 10. For example, the at least one external EM sensor 210 may be attached to a patient's solar plexus, navel, or nipples, but is not limited thereto.

The position and orientation information of the ultrasound probe 110 may be tracked using 3D position coordinate values and direction vector values of the at least one external EM sensor 210 and the EM sensor in the ultrasound probe 110 within an EM field generated by an EM field generator 220. According to an embodiment, the position and orientation information of the ultrasound probe 110 may be acquired and collected by a tracker.

The ultrasound imaging apparatus 100 may extract a region corresponding to a feature point on a patient's body from the pre-acquired image 320 from the other modality. According to an embodiment, the ultrasound imaging apparatus 100 may display '+' marker 322 in a region extracted from the pre-acquired image 320 from the other modality. According to an embodiment, the ultrasound imaging apparatus 100 may extract a region corresponding to a feature point on a patient's body from the pre-acquired image 320 from the other modality. According to another embodiment, the ultrasound imaging apparatus 100 may specify, based on a user input, a region in the pre-acquired image 320 from the other modality, which corresponds to a feature point on the patient's body.

The ultrasound imaging apparatus 100 may register the ultrasound image 310 and the pre-acquired image 320 from the other modality by using the position and orientation information of the ultrasound probe 110 acquired based on the 3D positional relationship ① between the at least one external EM sensor 210 and the EM sensor in the ultrasound probe 110 and a relationship ② between the region extracted from the pre-acquired image 320 from the other modality and the feature point on the actual patient's body. In this case, the registration may be the process of matching a position and an angle of the pre-acquired image 320 from the other modality to a position and an angle of the ultrasound image 310 to display together the ultrasound image 310 and the pre-acquired image 320 from the other modality, both images showing corresponding regions Any registration method known in the field of a medical image processing technology, including point-to-point registration, may be used for registration.

The ultrasound imaging apparatus 100 may display together the ultrasound image 310 and the pre-acquired image 320 from the other modality. According to an embodiment, the display 150 may display the ultrasound image 310 in a first region 150-1 and the pre-acquired image from the other modality registered with the ultrasound image 310 in a second region 150-2.

A general ultrasound imaging apparatus of the related art detects a position and an orientation of the ultrasound probe 110 via an EM sensor attached to the ultrasound probe 110 and performs image registration by manually or automatically aligning a position of the ultrasound image 310 with a position of the pre-acquired image 320 from the other modality in a point-to-point fashion. However, the registration method of the related art may require some user's intervention for image registration, in which case a high level of user expertise is required and registration accuracy is not high.

The ultrasound imaging apparatus 100 according to the disclosure may acquire 3D position information of the ultrasound probe 110, i.e., position and orientation information thereof, via the external EM sensor 210 attached to a feature point on the patient's body and extract a region corresponding to the feature point from the pre-acquired image 320 from the other modality and utilize the region for image registration, thereby increasing the accuracy of image registration. Furthermore, the image registration may be performed by simply attaching the at least one external EM sensor 210 onto the patient's body and accordingly, user convenience may be improved.

Figure 2:
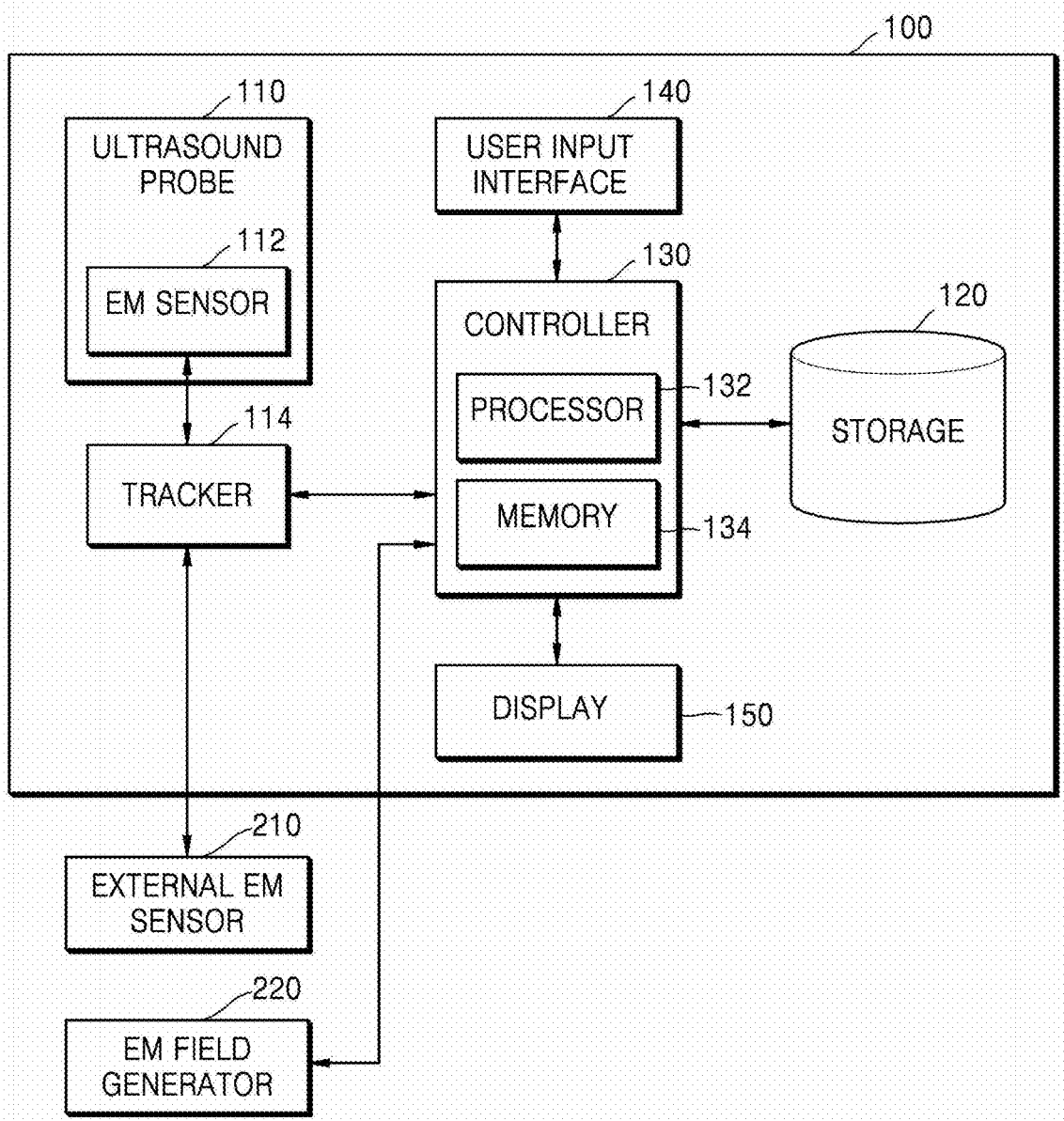
FIG. 2 is a block diagram of a configuration of an ultrasound imaging apparatus, according to an embodiment of the disclosure.

FIG. 2 is a block diagram of a configuration of an ultrasound imaging apparatus 100, according to an embodiment of the disclosure.

Referring to FIG. 2, the ultrasound imaging apparatus 100 may include an ultrasound probe 110, a tracker 114, a storage 120, a controller 130, a user input interface 140, and a display 150.

According to the disclosure, the ultrasound imaging apparatus 100 may receive ultrasound echo signals from the ultrasound probe 110 and perform image processing on the received echo signals to thereby generate an ultrasound image of an internal part of a patient's body. The ultrasound imaging apparatus 100 may be configured as a cart-type imaging apparatus, but is not limited thereto. For example, the ultrasound imaging apparatus 100 may be implemented as a portable-type ultrasound imaging apparatus including at least one of a Picture Archiving and Communication System (PACS) viewer, a smart phone, a laptop computer, a tablet PC, and a personal digital assistant (PDA).

According to an embodiment, the ultrasound imaging apparatus 100 may be connected by wire or wirelessly to an external EM sensor 210 and an EM field generator 220.

The ultrasound probe 110 may include a transducer that transmits an ultrasound signal to a patient's body and receive an ultrasound echo signal reflected from the patient's body. The ultrasound probe 110 may be connected to the ultrasound imaging apparatus 100 by wire or wirelessly. According to an embodiment, the ultrasound probe 110 may be a separate probe that is separated from the ultrasound imaging apparatus 100 and operates independently thereof.

The ultrasound probe 110 may include an EM sensor 112. The EM sensor 112 may be built into the ultrasound probe 110 but may be attached to one side of an outer surface of the ultrasound probe 110.

The tracker 114 may obtain 3D position coordinate values and direction vector values from the EM sensor 112 included in the ultrasound probe 110. In detail, the tracker 114 may track a position of the ultrasound probe 110 by using 3D position coordinate values and direction vector values of the EM sensor 112 and the external EM sensor 210 within an EM field generated by the EM field generator 220. According to an embodiment, the tracker 114 may set 3D position coordinate values of the external EM sensor 210 as a reference point and obtain 3D position coordinate values and direction vector values of the EM sensor 112 with respect to the set reference point. The tracker 114 may transmit the 3D position coordinate values and the direction vector values of the EM sensor 112 to the controller 120. The controller 130 may acquire position and orientation information of the ultrasound probe 110 by using the 3D position coordinate values and the direction vector values of the EM sensor 112, which are received from the tracker 114.

The storage 120 may store images of other modalities pre-acquired for a patient. According to an embodiment, the storage 120 may include at least one of a volatile memory (e.g., dynamic random access memory (DRAM), static RAM (SRAM), synchronous DRAM (SDRAM), etc.), a non-volatile memory (e.g., one time programmable read-only memory (OTPROM), PROM, erasable PROM (EPROM), electrically erasable PROM (EEPROM), mask ROM, flash ROM, etc.), a hard disk drive (HDD), and a solid state drive (SSD). In an embodiment, the storage 120 may include a database. The controller 130 may load pre-acquired images of other modalities from the storage 120.

The controller 130 may control all operations of the ultrasound probe 110, the tracker 114, the storage 120, the user input interface 140, and the display 150 and flow of signals among components within the ultrasound imaging apparatus 100. According to an embodiment, the controller 130 may control an operation of the EM field generator 220. The controller 130 may be configured as a hardware unit including a memory 134 for storing at least one of programs, algorithms, and data necessary for performing functions of the ultrasound imaging apparatus 100 and a processor 132 for processing the programs, the algorithms, or the data stored in the memory 134. For example, the controller 130 may be composed of the processor 132 including at least one of a central processing unit (CPU), a microprocessor, and a graphic processing unit (GPU).

The processor 132 may acquire position and orientation information of the ultrasound probe 110 based on a 3D positional relationship between the external EM sensor 210 attached to a first feature point on the patient's body and the EM sensor 112 included in the ultrasound probe 110, extract a second feature point corresponding to the first feature point from an image from another modality, and register an ultrasound image and the image from the other modality based on the position and orientation information of the ultrasound probe 110 with respect to a position of the external EM sensor 210 and a position of the second feature point extracted from the image from the other modality. The ultrasound imaging apparatus 100 may register the image from the other modality with the ultrasound image by using any registration method known in the field of a medical image processing technology, including point-to-point registration.

The processor 132 may load a pre-acquired image from another modality from the storage 120. However, embodiments are not limited thereto, and in an embodiment, the processor 132 may load a pre-acquired image from another modality from a PACS.

According to an embodiment, the processor 132 may set, as a reference point, the position of the external EM sensor 210 attached onto the first feature point that is a characteristic part of the patient's body and match a position and an angle of an image from another modality to those of an ultrasound image based on information about a distance and an angle between the reference point and the EM sensor 112 of the ultrasound probe 110.

According to an embodiment, the processor 132 may extract, from the image from the other modality, a second feature point having characteristics of a body structure corresponding to the first feature point on the patient's body by applying an image processing algorithm. The processor 132 may determine a position of the second feature point in the image from the other modality. The processor 132 may extract the second feature point based on at least one of a specific part of an object in the image from the other modality, an anatomical structure of the object therein, a resolution of the image from the other modality, and characteristics of the image from the other modality. However, embodiments are not limited thereto, and the processor 132 may extract a second feature point from the image from the other modality by using artificial intelligence (AI). For example, the processor 132 may extract the second feature point from the image from the other modality by using a known deep neural network (DNN) including at least one of a convolution neural network (CNN) and a recurrent neural network (RNN), or by using a machine learning model including a support vector machine (SVM). For example, when the first feature point is a solar plexus that is one of a patient's body structures, the processor 132 may determine a position and a boundary of a part corresponding to the solar plexus in the image from the other modality and extract the part corresponding to the solar plexus.

In another embodiment, the processor 132 may determine a position of the second feature point in the image from the other modality based on a user input received via the user input interface 140.

According to an embodiment, the processor 132 may correct a registration error that occurs due to a difference of the position and angle between the second feature point extracted from the image from the other modality and the external EM sensor 210 attached onto a patient's body surface. The processor 132 may correct the position of the second feature point based on a minimum distance between the position of the second feature point extracted from the image from the other modality and a body surface depicted in the image from the other modality. According to another embodiment, the processor 132 may correct a position and an angle of the second feature point based on a relationship of a distance and an angle between the position of the second feature point extracted from the image from the other modality and the body surface in the image from the other modality. A detailed description thereof will be set forth below with reference to FIGS. 6B and 6C.

The user input interface 140 may receive a user input for manipulating the ultrasound imaging apparatus 100 while capturing an ultrasound image of the patient. The user input interface 140 may be configured as a control panel including hardware components such as a keypad, a mouse, a trackball, a touch pad, and a jog switch, but is not limited thereto. In an embodiment, the user input interface 140 may be configured as a touch screen for receiving a touch input and displaying a graphical user interface (GUI).

The user input interface 140 may receive a user input for selecting, from the image from the other modality, a position corresponding to a first feature point on a patient's body. For example, when the first feature point is a patient's solar plexus, the user input interface 140 may receive a user input for selecting a part corresponding to the solar plexus in a CT image.

The display 150 may display an ultrasound image together with an image from another modality. According to an embodiment, the display 150 may display, according to control by the controller 130, an ultrasound image in a first region and an image from another modality registered with the ultrasound image in a second region. However, a method whereby the display 150 displays an ultrasound image and an image from another modality is not limited as described above. In an embodiment, the display 150 may display the ultrasound image and the image from the other modality in such a manner that they overlap while being registered with each other, or in such a manner that they are arranged side by side in the vertical direction.

For example, the display 150 may be formed as a physical device including at least one of a cathode-ray tube (CRT) display, a liquid crystal display (LCD), a plasma display panel (PDP), an organic light-emitting diode (OLED) display, a field emission display (FED), a LED display, a vacuum fluorescent display (VFD), a digital light processing (DLP) display, a flat panel display (FPD), a 3D display, and a transparent display, but is not limited thereto. In an embodiment, the display 150 may be formed as a touch screen including a touch interface. When the display 150 is configured as a touch screen, the display 150 may be a component integrated with the user input interface 140 configured as a touch panel.

According to an embodiment, the display 150 may display, in an ultrasound image, a first marker indicating a position of a first feature point on a patient's body in the ultrasound image while displaying, in an image from another modality, a second marker indicating a position of a second feature point extracted from the image from the other modality. A specific embodiment thereof will be described in detail below with reference to FIG. 4.

According to an embodiment, the display 150 may display a GUI indicating a signal strength of each external EM sensor 210 attached onto the patient's body. A specific embodiment thereof will be described in detail below with reference to FIG. 8.

The external EM sensor 210 may be attached by the user to a specific part on the patient's body. The external EM sensor 210 may be composed of one or more EM sensors. The external EM sensor 210 may be attached by the user to a characteristic part on the patient's body. For example, the external EM sensor 210 may be attached to a specific part representing characteristics of a patient's body structure such as a solar plexus, a naval, or nipples. The tracker 114 may acquire information about 3D position coordinate values and direction vector values of the external EM sensor 210 in an EM field generated by the EM field generator 220, and transmit the acquired information to the controller 130.

The EM field generator 220 may be located adjacent to the ultrasound probe 110 and the external EM sensor 210 and create an EM field in a predetermined range of a region surrounding the patient's body. A 3D coordinate system may be created by the EM field generator 220 in a region where the ultrasound probe 110 and the external EM sensor 210 are located.

Figure 3:
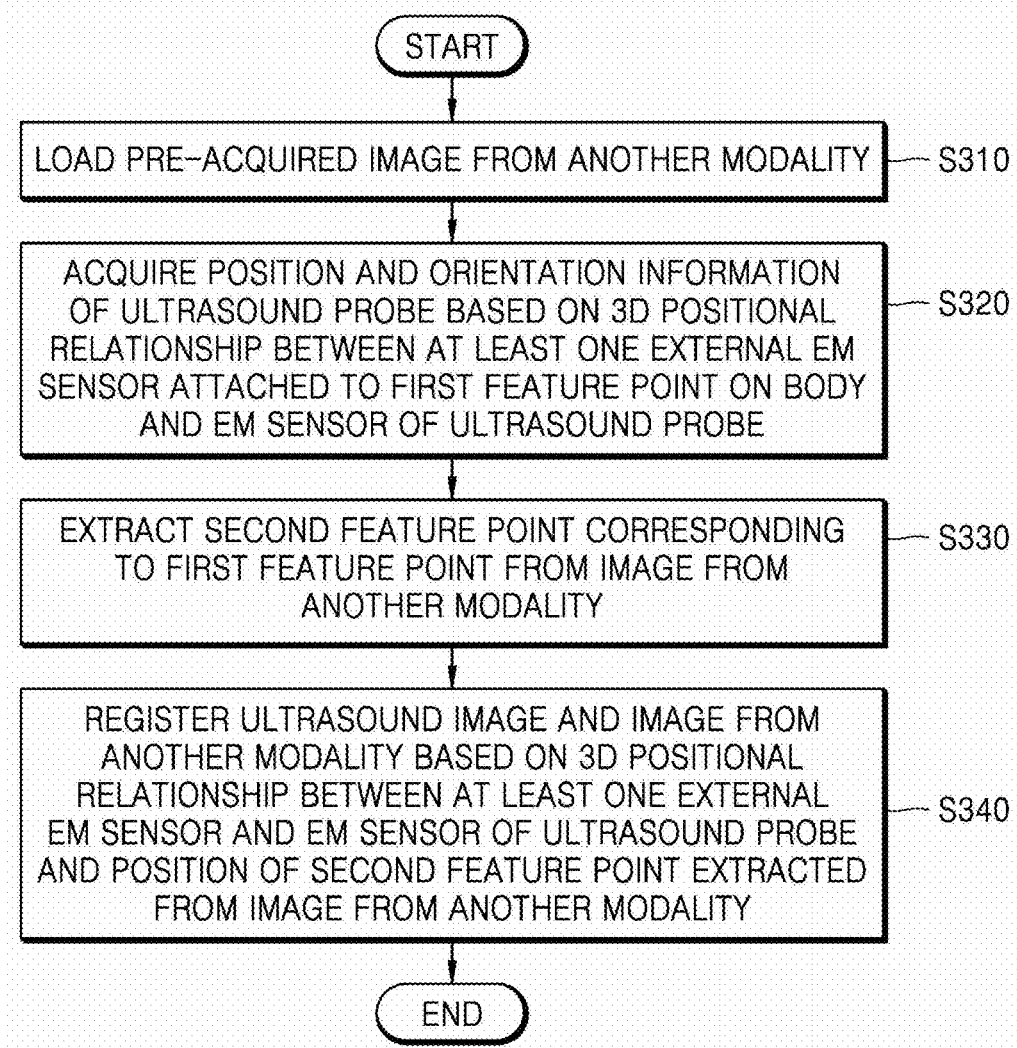
FIG. 3 is a flowchart of a method, performed by an ultrasound imaging apparatus, of registering an ultrasound image and an image from another modality, according to an embodiment of the disclosure.

FIG. 3 is a flowchart of a method, performed by an ultrasound imaging apparatus, of registering an ultrasound image and an image from another modality, according to an embodiment of the disclosure.

The ultrasound imaging apparatus loads a pre-acquired image from another modality (operation S310). An image from another modality acquired from a patient, such as an MR image or CT image, may be stored in the storage (120 of FIG. 2) of the ultrasound imaging apparatus. In an embodiment, the ultrasound imaging apparatus may load the image from the other modality stored in the storage 120. According to another embodiment, the ultrasound imaging apparatus may load, from a PACS, the image from the other modality pre-acquired for the patient.

The ultrasound imaging apparatus acquires position and orientation information of an ultrasound probe based on a 3D positional relationship between at least one external EM sensor attached to a first feature point on a patient's body and an EM sensor of the ultrasound probe (operation S320). According to an embodiment, the ultrasound imaging apparatus may set, as a reference point, a position of the at least one external EM sensor attached onto the first feature point that is a characteristic part of the patient's body, obtain 3D position coordinate values and direction vector values of the ultrasound probe based on information about a distance and an angle between the reference point and the EM sensor of the ultrasound probe, and track a position of the ultrasound probe by using the 3D position coordinate values and the direction vector values of the ultrasound probe. The ultrasound imaging apparatus may define, as a transform matrix, a relationship between the 3D position coordinate values of the ultrasound probe and 3D position coordinate values of the at least one external EM sensor attached onto the patient's body.

The ultrasound imaging apparatus extracts, from the image from the other modality, a second feature point corresponding to the first feature point (operation S330). According to an embodiment, the ultrasound imaging apparatus may extract a second feature point having characteristics of a body structure corresponding to the first feature point on the patient's body by applying an image processing algorithm. For example, when the first feature point is a solar plexus that is one of a patient's body structures, the ultrasound imaging apparatus may extract a position and a boundary of a part corresponding to the solar plexus in the image from the other modality. In another embodiment, the ultrasound imaging apparatus may determine a position of the second feature point in the image from the other modality based on a user input.

According to an embodiment, the ultrasound imaging apparatus may define, as a second transform matrix, a relationship between the 3D position coordinate values of the at least one external EM sensor attached onto the patient's body and position coordinate values of the second feature point extracted from the image from the other modality.

The ultrasound imaging apparatus registers an ultrasound image and the image from the other modality based on the 3D positional relationship between the at least one external EM sensor and the EM sensor of the ultrasound probe and the position of the second feature point extracted from the image from the other modality (operation S340). According to an embodiment, the ultrasound imaging apparatus may register the image from the other modality with the ultrasound image by using any registration method known in the field of a medical image processing technology, including point-to-point registration. According to an embodiment, the ultrasound imaging apparatus may generate a third transform matrix defining a relationship between a position and an orientation of the ultrasound probe and a position and an orientation of the image from the other modality by merging the first transform matrix defined in operation S320 and the second transform matrix defined in operation S330. The ultrasound imaging apparatus may register the image from the other modality with the ultrasound image by using the third transform matrix generated by merging the first and second transform matrices.

Figure 4:
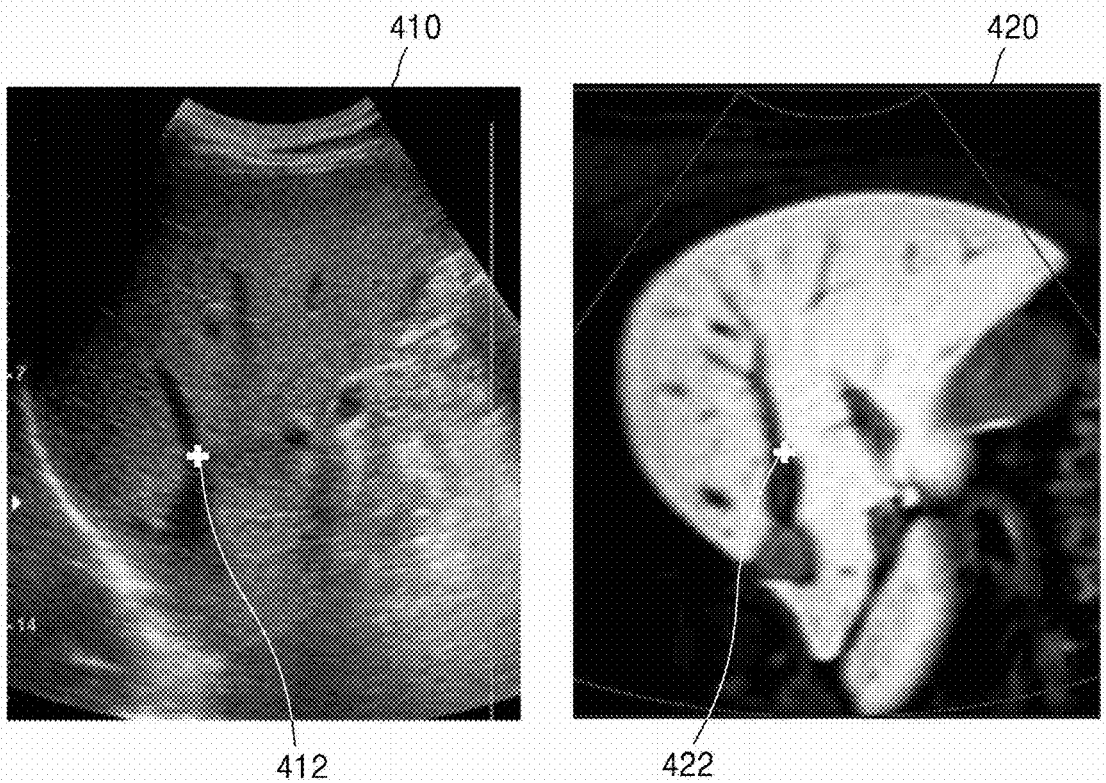
FIG. 4 illustrates an example in which an ultrasound imaging apparatus registers an ultrasound image and an image from another modality, according to an embodiment of the disclosure.

FIG. 4 illustrates an example in which an ultrasound imaging apparatus registers an ultrasound image and an image from another modality, according to an embodiment of the disclosure.

Referring to FIG. 4, the ultrasound imaging apparatus may perform image registration to match a position and an angle of a CT image 420 to a position and an angle of an ultrasound image 410. According to an embodiment, the ultrasound imaging apparatus may register the ultrasound image 410 and the CT image 420 by using a 3D positional relationship between an ultrasound probe and an external EM sensor attached to a feature point on a patient's body during acquisition of the ultrasound image 420 and a position of a feature point 422 extracted from the CT image 420.

According to an embodiment, the ultrasound imaging apparatus may register two images, i.e., the ultrasound image 410 and the CT image 420, by using point-to-point registration between first and second feature points 412 and 422 respectively extracted from the ultrasound image 410 and the CT image 420, but embodiments are not limited thereto. Any registration method known in the art may be applied to a medical imaging apparatus according to the disclosure.

According to an embodiment, the ultrasound imaging apparatus may display a marker (+) indicating a position of the first feature point 412 in the ultrasound image 410 and display a marker '+' indicating a position of the second feature point 422 in the CT image 420 registered with the ultrasound image 410. In the embodiment shown in FIG. 4, the marker '+' is used to display a reference point for registration between the ultrasound image 410 and the CT image 420 via a GUI element, thereby allowing a user to intuitively identify the reference point for registration.

FIG. 5 illustrates an example of a UI via which an ultrasound imaging apparatus instructs a user to attach an external electromagnetic (EM) sensor to a specific part of a patient's body, according to an embodiment of the disclosure.

Referring to FIG. 5, the ultrasound imaging apparatus may display on a display 500 a UI for instructing the user to place an external EM sensor 530 on a specific body part of a patient 10.

The ultrasound imaging apparatus may extract a feature point from an image from another modality, such as an MR image or a CT image, which is pre-acquired for an object and loaded from the storage (120 of FIG. 2) or a PACS. In an embodiment, the ultrasound imaging apparatus may extract a feature point based on at least one of a specific part of the object in the image from the other modality, an anatomical structure of the object therein, a resolution of the image from the other modality, and characteristics of the image from the other modality. However, embodiments are not limited thereto, and the ultrasound imaging apparatus may extract a feature point from the image from the other modality by using AI. For example, the ultrasound imaging apparatus may extract a feature point from the image from the other modality by using a known DNN including at least one of a CNN and a RNN, or by using a machine learning model such as a SVM.

According to an embodiment, the ultrasound imaging apparatus may display on the display 500 a UI for instructing the user to place the external EM sensor 530 on a specific part corresponding to a feature point extracted from an actual patient's body. The UI displayed on the display 500 may include a human body model UI 510 schematizing a human body shape and a sensor UI 520 schematizing the shape of the external EM sensor 530. For example, when the ultrasound imaging apparatus extracts a 'solar plexus' as a feature point from the image from the other modality, the display 500 may display a message, such as 'Place a sensor on the solar plexus', which instructs the user to place the external EM sensor 530 on a specific body part (e.g., the solar plexus) of the patient 10.

The ultrasound imaging apparatus may display a UI for instructing the user to place the external EM sensor 530 not only at a specific position on a patient's body but also in a predetermined direction. The external EM sensor 530 has not only 3D position coordinate values but also direction vector values in an EM field generated by the EM field generator (220 of FIG. 2). Thus, when the user places the external EM sensor 530 in a wrong direction other than the predetermined direction, the accuracy of image registration may be degraded.

Figure 6A:
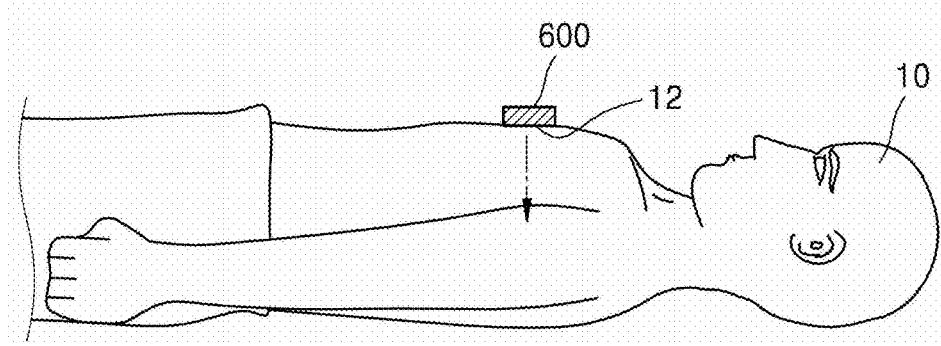
FIG. 6A illustrates an external EM sensor attached to a specific body part of a patient.

FIG. 6A illustrates an external EM sensor 600 attached to a specific body part 12 of a patient 10.

The external EM sensor 600 may be attached by the user to the characteristic body part 12 of the patient 10. In the embodiment shown in FIG. 6A, the external EM sensor 600 may be attached to a solar plexus of the patient 10. Because the external EM sensor 600 is attached onto a patient's body surface, a position of the external EM sensor 600 does not match a position of a feature point extracted from an actually captured image from another modality, and accordingly, an error occurs during registration due to the difference.

Figure 6B:
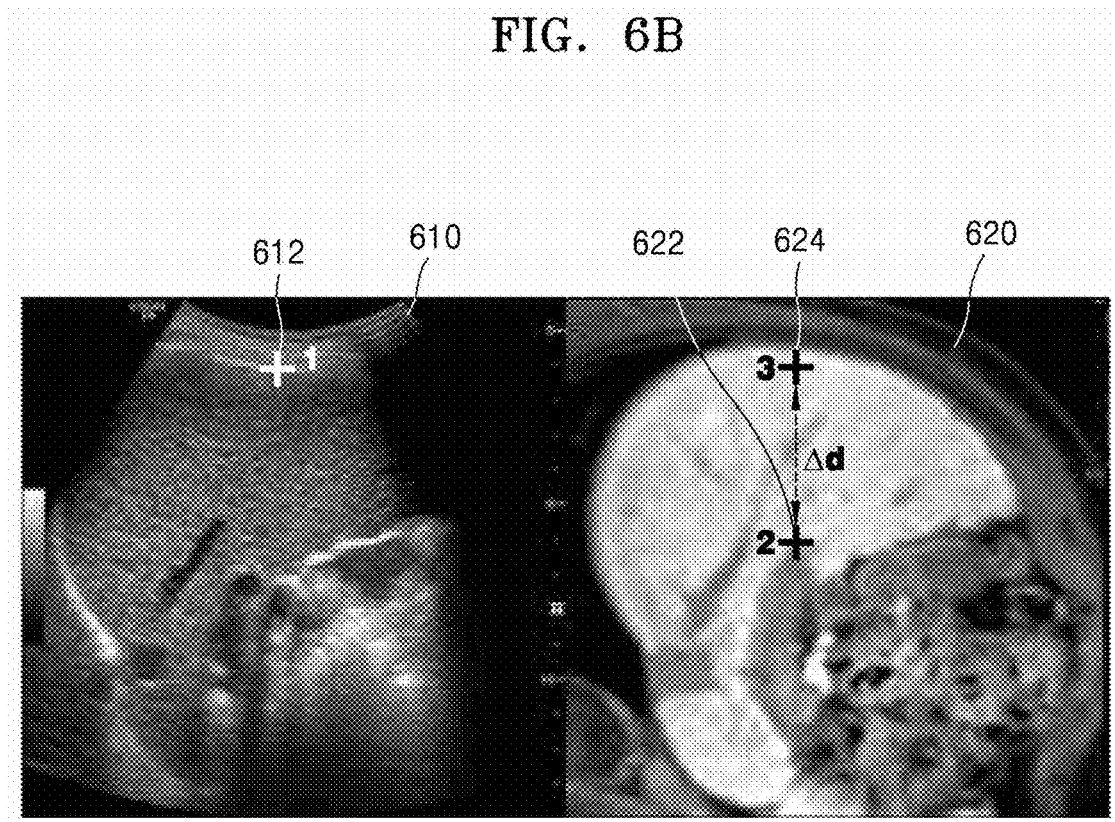
FIG. 6B illustrates an example in which an ultrasound imaging apparatus corrects a registration error due to a position of an external EM sensor, according to an embodiment of the disclosure.

FIG. 6B illustrates an example in which the ultrasound imaging apparatus corrects a registration error due to a position of the external EM sensor (600 of FIG. 6A), according to an embodiment of the disclosure.

Referring to FIG. 6B, the ultrasound imaging apparatus may extract, from an image 620 from another modality, a second feature point 622 corresponding to the characteristic body part (12 of FIG. 6A) of the patient (10 of FIG. 6A) to which the external EM sensor (600 of FIG. 6A) is attached. According to an embodiment, the ultrasound imaging apparatus may extract, from the image 620 from the other modality, a second feature point 622 corresponding to the characteristic body part 12 of the patient 10 by applying an image processing algorithm. According to another embodiment, the ultrasound imaging apparatus may determine a position of the second feature point 622 in the image 620 from the other modality based on a received user input.

The position of the second feature point 622 extracted by the ultrasound imaging apparatus from the image 620 from the other modality may not match a corresponding position acquired via the external EM sensor 600 attached to the characteristic body part 12 of the actual patient 10. As described above, because the external EM sensor 600 is attached onto a patient's body surface, the position of the external EM sensor 600 may not match the position of the second feature point 622 extracted from the image 620 from the other modality actually captured.

The ultrasound imaging apparatus may correct the position of the second feature point 622 extracted from the image 620 from the other modality to a third feature point 624 in order to compensate for a registration error generated due to a difference between the position of the characteristic body part 12 of the patient 10, acquired via the external EM sensor 600, and the position of the second feature point 622. The ultrasound imaging apparatus may correct the position of the second feature point 622 extracted from the image 620 from the other modality by adjusting it to a position on a body surface in the image 620 from the other modality in order to precisely reflect the position of the external EM sensor 600 that may be placed on an actual patient's body. According to an embodiment, the ultrasound imaging apparatus may calculate a minimum distance Δd between the position of the second feature point 622 extracted from the image 620 from the other modality and the body surface in the image 620 of the other modality and correct the position of the second feature point 622 to the third feature point 624 by moving the second feature point 622 by the minimum distance Δd. According to an embodiment, the ultrasound imaging apparatus may correct the position of the second feature point 622 to the third feature point 624 by moving the second feature point 622 by the minimum distance Δd along a depth direction of a rectangular coordinate system.

The ultrasound imaging apparatus may obtain 3D position coordinate values and direction vector values of an ultrasound probe by using the external EM sensor 600 attached to the characteristic body part 12 of the patient 10 as a reference point, and the ultrasound image 610 and display a first feature point 612 in the ultrasound image 610 corresponding to the reference point. The first feature point 612 may be a region in the ultrasound image 610 corresponding to the characteristic body part 12 of the patient 10.

The ultrasound imaging apparatus may register the ultrasound image 610 and the image 620 from the other modality by using the first feature point 612 and the third feature point 624 obtained by correcting the error in the image 620 from the other modality. In an embodiment, the ultrasound imaging apparatus may register the ultrasound image 610 and the image 620 from the other modality by using any registration method known in the field of a medical image processing technology, including point-to-point registration.

Figure 6C:
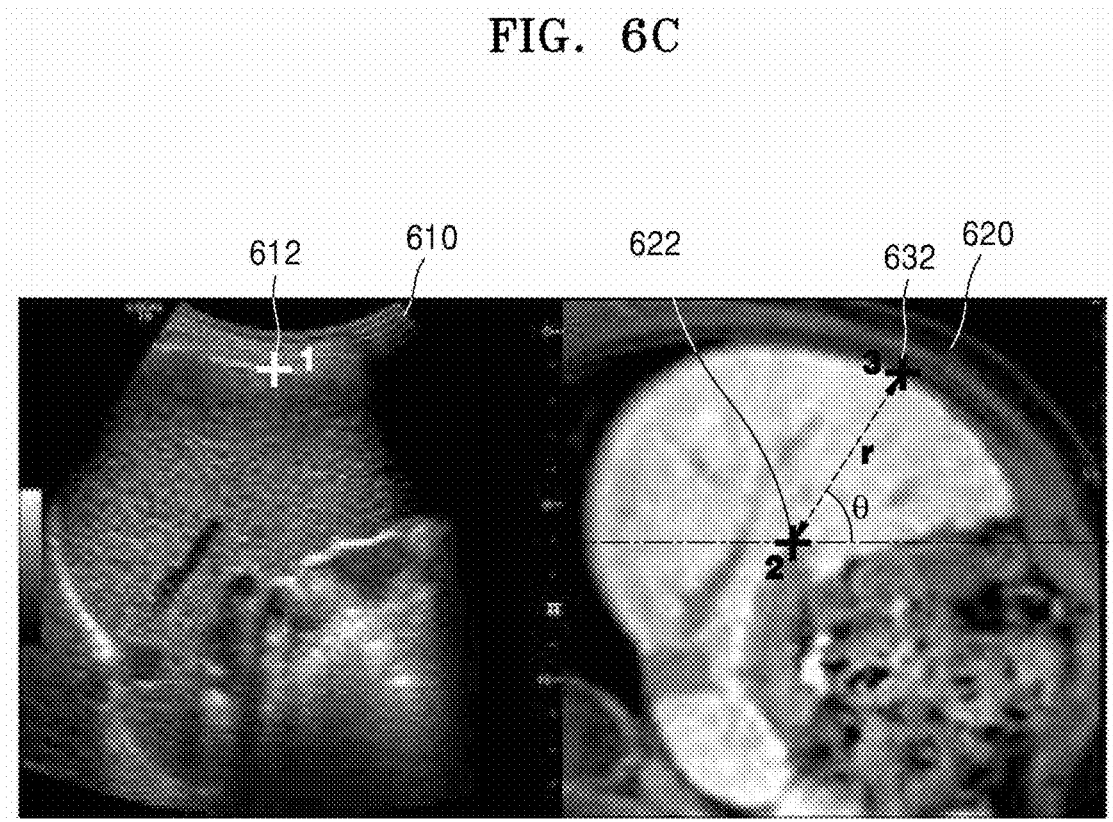
FIG. 6C illustrates an example in which the ultrasound imaging apparatus corrects a registration error by taking into account a position and an angle at which the external EM sensor is attached onto a body surface, according to an embodiment of the disclosure.

FIG. 6C illustrates an example in which the ultrasound imaging apparatus corrects a registration error by taking into account a position and an angle at which the external EM sensor (600 of FIG. 6A) is attached onto a body surface, according to an embodiment of the disclosure.

FIG. 6C illustrates an embodiment in which the ultrasound imaging apparatus corrects a position of a second feature point 622 extracted from an image 620 from another modality when the external EM sensor 600 is attached to a body part having a non-planar surface, such as an arm or leg, unlike in the embodiment shown in FIG. 6B. Referring to FIG. 6C, the ultrasound imaging apparatus may extract, from the image 620 from the other modality, the second feature point 622 corresponding to the characteristic body part (12 of FIG. 6A) of the patient (10 of FIG. 6A) to which the external EM sensor 600 is attached. When the external EM sensor 600 is attached to a cylindrical body part having a rounded surface, such as an arm or leg, the position of the second feature point 622 extracted from the image 620 from the other modality may not match a position of the external EM sensor 600 attached onto the actual body surface.

The ultrasound imaging apparatus may correct the position of the second feature point 622 extracted from the image 620 from the other modality to a third feature point 632 in order to compensate for a registration error generated due to a difference between the position of the characteristic body part 12 of the patient 10, acquired via the external EM sensor 600, and the position of the second feature point 622. According to an embodiment, the ultrasound imaging apparatus may calculate a distance r and an angle θ between the position of the second feature point 622 extracted from the image 620 from the other modality and a body surface in the image 620 from the other modality and correct the position of the second feature point 622 to the third feature point 632 based on the calculated distance r and angle θ. For example, the ultrasound imaging apparatus may correct the position of the second feature point 622 in the image 620 from the other modality to the third feature point 632 by using a polar coordinate system.

A method of registering images from different modalities after correction is substantially the same as the method described with reference to FIG. 6B, and thus a detailed description thereof will not be repeated below.

Figure 7:
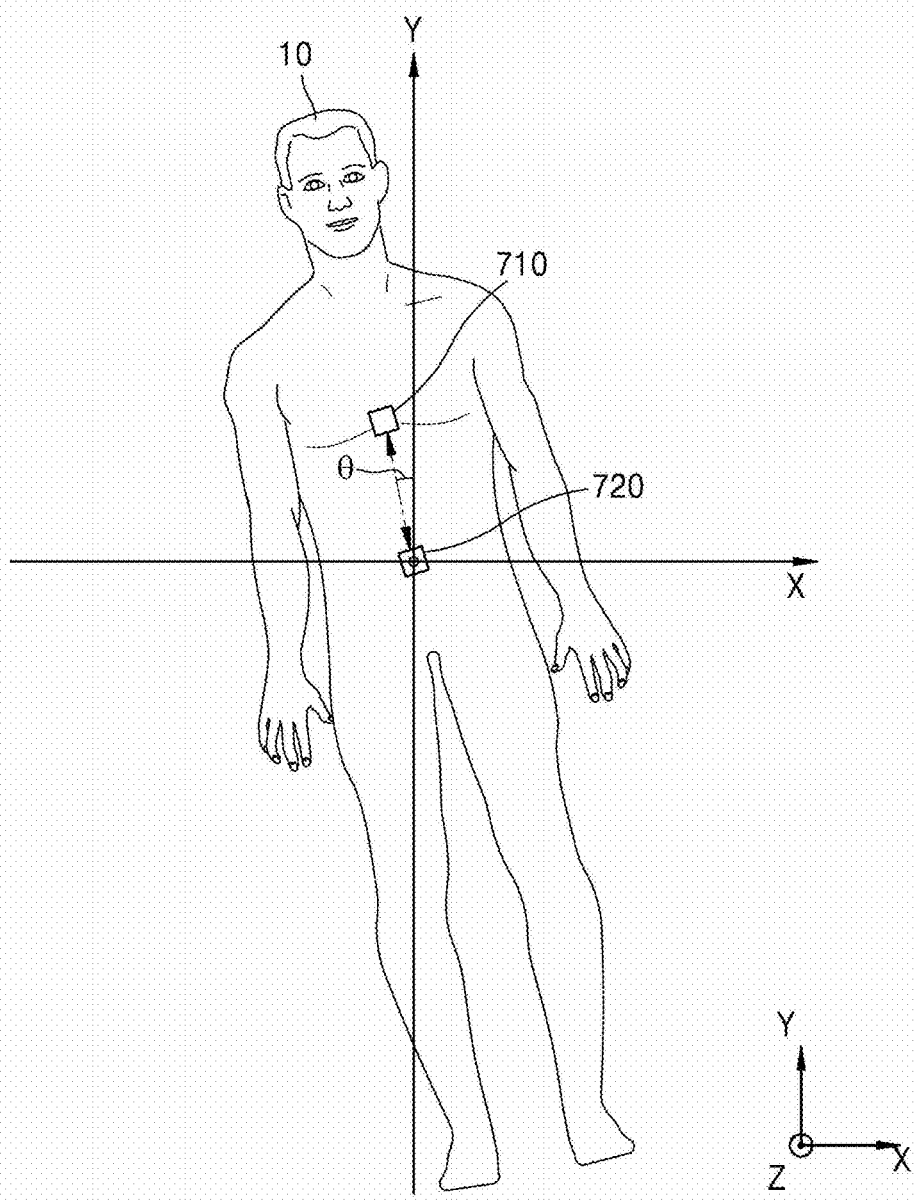
FIG. 7 illustrates an example in which an ultrasound imaging apparatus corrects a registration angular error by using an external EM sensor attached to a patient's body, according to an embodiment of the disclosure.

FIG. 7 illustrates an example in which an ultrasound imaging apparatus corrects a registration angular error by using an external EM sensor attached to a patient's body, according to an embodiment of the disclosure.

Referring to FIG. 7, the ultrasound imaging apparatus may correct an angular error in image registration based on an angle between a plurality of external EM sensors, i.e., first and second external EM sensors 710 and 720, attached onto a body of a patient 10. The first and second external EM sensors 710 and 720 may be attached by the user onto a characteristic part of the patient's body. For example, the first and second external EM sensors 710 and 720 may be respectively arranged on a solar plexus and a naval of the patient 10.

The ultrasound imaging apparatus may calculate an angle θ between a virtual line connecting the first and second external EM sensors 710 and 720 and a straight line in a y-axis direction. According to an embodiment, the ultrasound imaging apparatus may recognize at which angle the patient 10 is lying in a specific direction based on the calculated angle θ and perform image registration by correcting an angular error by the calculated angle θ.

Figure 8:
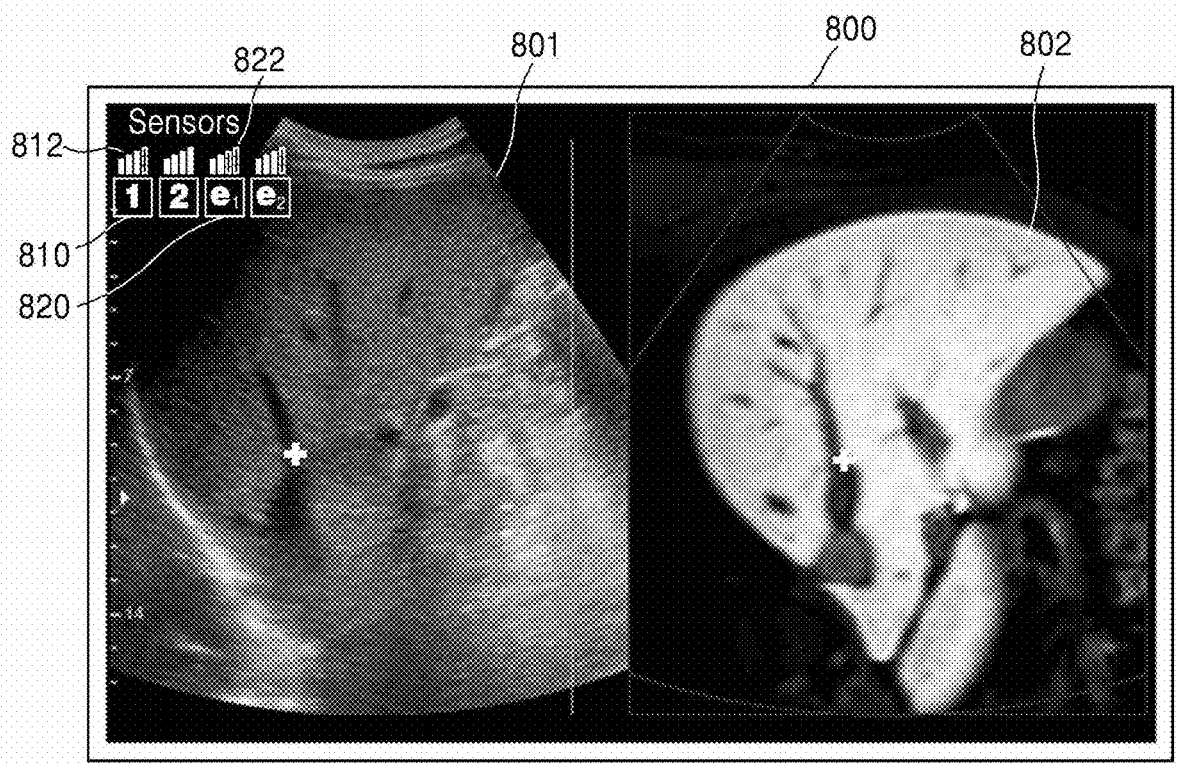
FIG. 8 illustrates a UI via which an ultrasound imaging apparatus displays a sensitivity of each of an EM sensor in an ultrasound probe and an external EM sensor attached to a patient's body.

FIG. 8 illustrates a UI via which an ultrasound imaging apparatus displays a sensitivity of each of an EM sensor in an ultrasound probe and an external EM sensor attached to a patient's body.

Referring to FIG. 8, the ultrasound imaging apparatus may display an ultrasound image 801 in a first region of a display 800 and an image 802 from another modality registered with the ultrasound image 801 in a second region of the display 800.

The ultrasound imaging apparatus may display, on one side of the display 800, a GUI indicating signal sensitivities of an EM sensor 810 of an ultrasound probe and at least one external EM sensor 820. According to an embodiment, a signal strength UI 812 for the EM sensor 810 of the ultrasound probe may be a GUI represented by the number of bars similar to the manner of representing antenna sensitivity. Similarly, a signal strength UI 822 for the external EM sensor 820 may also be a GUI represented by the number of bars.

The signal strength UIs 812 and 822 shown in FIG. 8 for displaying sensor sensitivities may allow the user to intuitively identify signal sensitivities of the external EM sensor 820 attached to the patient's body as well as the EM sensor 810 of the ultrasound probe.

FIG. 9A illustrates a plurality of external EM sensors attached onto a patient's body.

Referring to FIG. 9A, first and second external EM sensors 901 and 902 may be attached to a characteristic body part of a patient 10. In an embodiment, the first and second external EM sensors 901 and 902 may be respectively attached to first and second feature points of the patient's body. For example, the first and second external EM sensors 901 and 902 may be respectively attached to a solar plexus and a naval of the patient 10.

The first external EM sensor 901 and the second external EM sensor 902 may each have three-dimensional position coordinate values and direction vector values in an EM field generated by the EM field generator (220 of FIG. 2), and a vector connecting the first and second external EM sensors 901 and 902 may be defined.

Figure 9C:
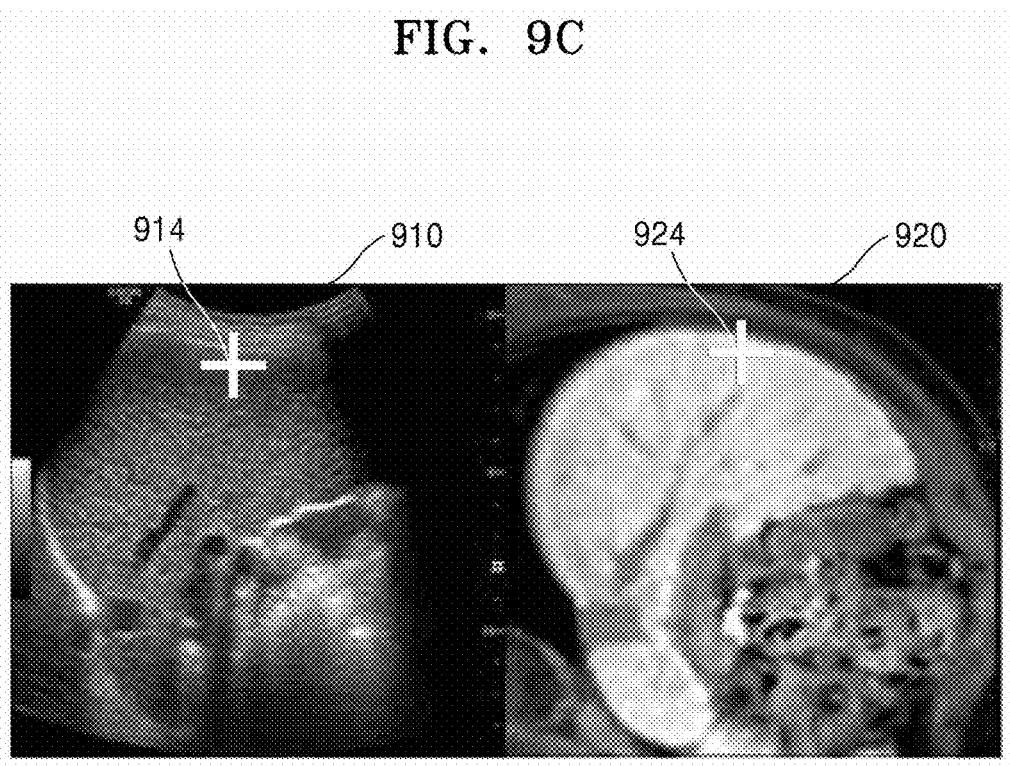
FIG. 9C illustrates an example in which an ultrasound imaging apparatus registers an ultrasound image and the image from the other modality, according to an embodiment of the disclosure.

FIG. 9B illustrates an example in which an ultrasound imaging apparatus extracts first and second feature points 921 and 922 from an image 920 from another modality, according to an embodiment of the disclosure, and FIG. 9C illustrates an example in which the ultrasound imaging apparatus registers an ultrasound image 910 and the image 920 from the other modality, according to an embodiment of the disclosure.

Referring to FIG. 9B, the ultrasound imaging apparatus may extract the first and second feature points 921 and 922 respectively corresponding to positions of the first and second external EM sensors 901 and 902 from the image 920 from the other modality. According to an embodiment, the ultrasound imaging apparatus may extract the positions of the first and second feature points 921 and 922 from the image 920 from the other modality by applying an image processing algorithm. According to another embodiment, the ultrasound imaging apparatus may determine the positions of the first and second feature points 921 and 922 based on a user input.

Referring to FIG. 9C, the ultrasound imaging apparatus may extract a third feature point 924 based on the first and second feature points (921 and 922 of FIG. 9B) extracted from the image 920 from the other modality and register the ultrasound image 910 and the image 920 from the other modality based on a position of the extracted third feature point 924 and a 3D positional relationship among an ultrasound probe and the first and second external EM sensors (901 and 902 of FIG. 9A). According to an embodiment, the ultrasound imaging apparatus may display a plus-shaped marker '+' at the position of the third feature point 924 extracted from the image 920 from the other modality. According to an embodiment, the ultrasound imaging apparatus may display a plus-shaped marker '+' at a position of a feature point 914 corresponding to the third feature point 924 in the ultrasound image 910.

Although not shown in FIG. 9C, the ultrasound imaging apparatus may also extract, from the ultrasound image 910, a plurality of feature points respectively corresponding to the first and second feature points 921 and 922 extracted from the image 920 from the other modality, and perform image registration by using positions of the feature points extracted from the ultrasound image 910 and the first and second feature points 921 and 922 extracted from the image 920 from the other modality.

Figure 10:
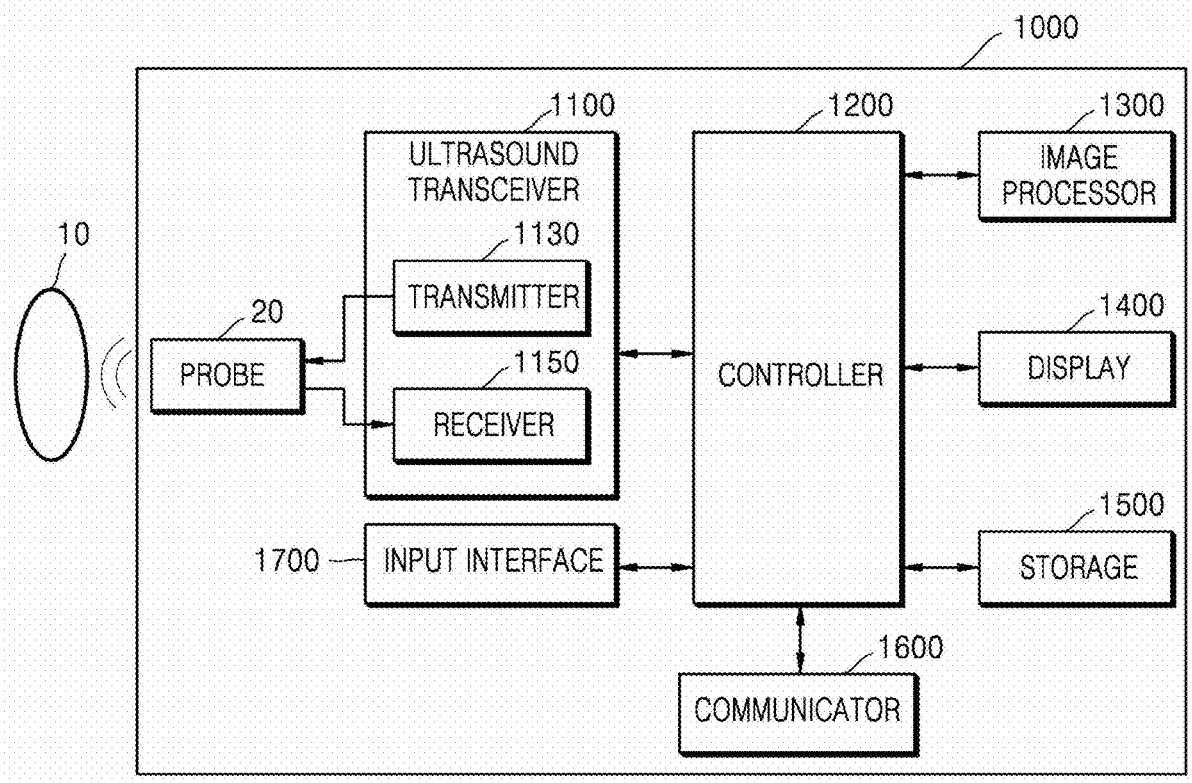
FIG. 10 is a block diagram of a configuration of an ultrasound imaging apparatus, according to an embodiment of the disclosure.

FIG. 10 is a block diagram illustrating a configuration of an ultrasound imaging apparatus 1000, i.e., a diagnostic apparatus, according to an exemplary embodiment.

Referring to FIG. 10, the ultrasound imaging apparatus 1000 may include a probe 20, an ultrasound transceiver 1100, a controller 1200, an image processor 1300, one or more displays 1400, a storage 1500, e.g., a memory, a communicator 1600, i.e., a communication device or an interface, and an input interface 1700.

The ultrasound imaging apparatus 1000 may be of a cart-type or a portable-type ultrasound imaging apparatus, that is portable, moveable, mobile, or hand-held. Examples of the portable-type ultrasound imaging apparatus 1000 may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 1130. The plurality of transducers may receive ultrasound signals reflected from the object 10 to generate reception signals. In addition, the probe 20 and the ultrasound imaging apparatus 1000 may be formed in one body (e.g., disposed in a single housing), or the probe 20 and the ultrasound imaging apparatus 1000 may be formed separately (e.g., disposed separately in separate housings) but linked wirelessly or via wires. In addition, the ultrasound imaging apparatus 1000 may include one or more probes 20 according to embodiments.

The controller 1200 may control the transmitter 1130 for the transmitter 1130 to generate transmitting signals to be applied to each of the plurality of transducers based on a position and a focal point of the plurality of transducers included in the probe 20.

The controller 1200 may control the ultrasound receiver 1150 to generate ultrasound data by converting reception signals received from the probe 20 from analogue to digital signals and summing the reception signals converted into digital form, based on a position and a focal point of the plurality of transducers.

The image processor 1300 may generate an ultrasound image by using ultrasound data generated from the ultrasound receiver 1150.

The display 1400 may display a generated ultrasound image and various pieces of information processed by the ultrasound imaging apparatus 1000. The ultrasound imaging apparatus 1000 may include two or more displays 1400 according to the present exemplary embodiment. The display 1400 may include a touch screen in combination with a touch panel.

The controller 1200 may control the operations of the ultrasound imaging apparatus 1000 and flow of signals between the internal elements of the ultrasound imaging apparatus 1000. The controller 1200 may include a memory for storing a program or data to perform functions of the ultrasound imaging apparatus 1000 and a processor and/or a microprocessor (not shown) for processing the program or data. For example, the controller 1200 may control the operation of the ultrasound imaging apparatus 1000 by receiving a control signal from the input interface 1700 or an external apparatus.

The ultrasound imaging apparatus 1000 may include the communicator 1600 and may be connected to external apparatuses, for example, servers, medical apparatuses, and portable devices such as smart phones, tablet personal computers (PCs), wearable devices, etc., via the communicator 1600.

The communicator 1600 may include at least one element capable of communicating with the external apparatuses. For example, the communicator 1600 may include at least one among a short-range communication module, a wired communication module, and a wireless communication module.

The communicator 1600 may receive a control signal and data from an external apparatus and transmit the received control signal to the controller 1200 so that the controller 1200 may control the ultrasound imaging apparatus 1000 in response to the received control signal.

The controller 1200 may transmit a control signal to the external apparatus via the communicator 1600 so that the external apparatus may be controlled in response to the control signal of the controller 1200.

For example, the external apparatus connected to the ultrasound imaging apparatus 1000 may process the data of the external apparatus in response to the control signal of the controller 1200 received via the communicator 1600.

A program for controlling the ultrasound imaging apparatus 1000 may be installed in the external apparatus. The program may include command languages to perform part of operation of the controller 1200 or the entire operation of the controller 1200.

The program may be pre-installed in the external apparatus or may be installed by a user of the external apparatus by downloading the program from a server that provides applications. The server that provides applications may include a recording medium where the program is stored.

The storage 1500 may store various data or programs for driving and controlling the ultrasound imaging apparatus 1000, input and/or output ultrasound data, ultrasound images, applications, etc.

The input interface 1700 may receive a user's input to control the ultrasound imaging apparatus 1000 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound imaging apparatus 1000 according to the present exemplary embodiment is described below with reference to FIGS. 11A, 11B, and 11C.

Figure 11A:
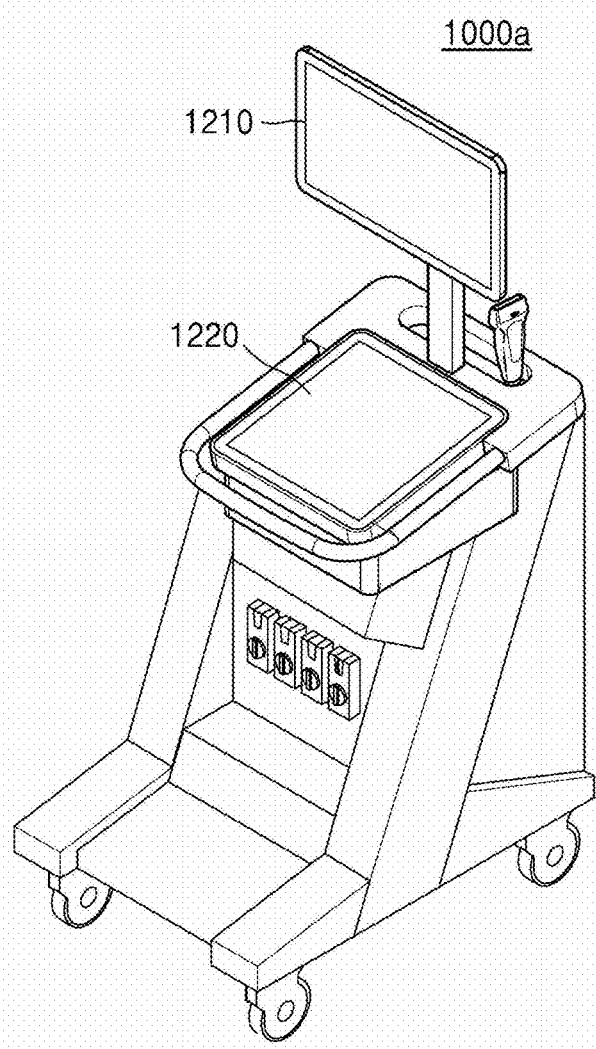
FIGS. 11A through 11C illustrate ultrasound imaging apparatuses according to embodiments of the disclosure.
Figure 11B:
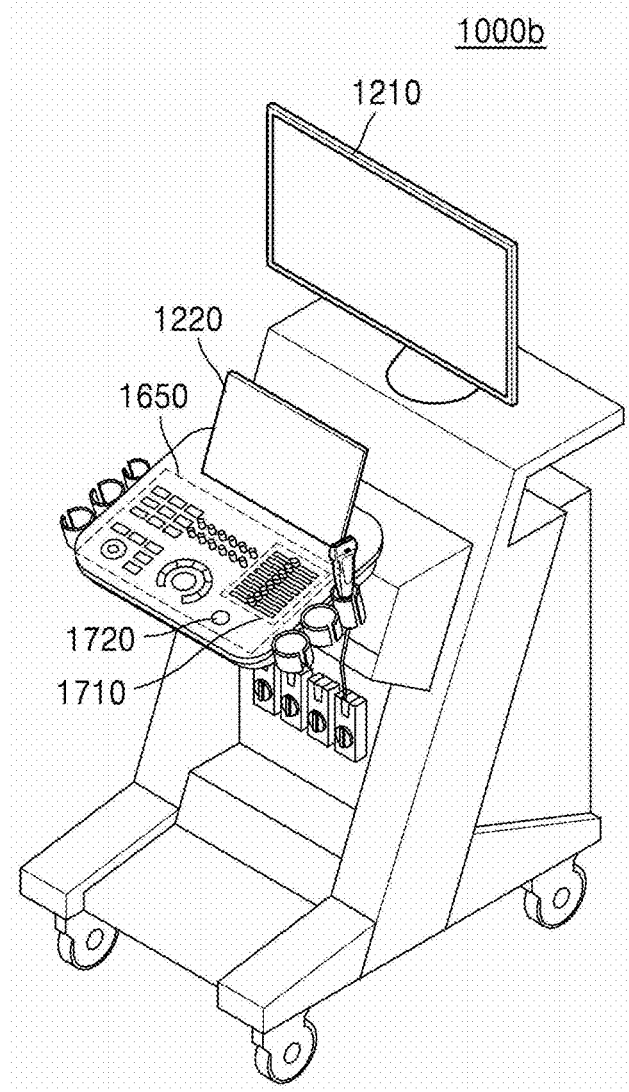
Figure 11C:
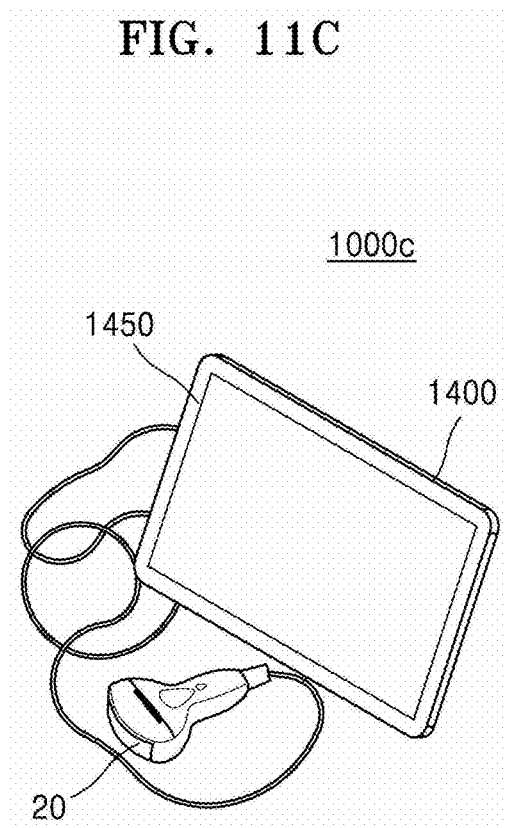

FIGS. 11A, 11B, and 11C are diagrams illustrating ultrasound imaging apparatus according to an exemplary embodiment.

Referring to FIGS. 11A and 11B, the ultrasound imaging apparatuses 1000a and 1000b may include a main display 1210 and a sub-display 1220. At least one among the main display 1210 and the sub-display 1220 may include a touch screen. The main display 1210 and the sub-display 1220 may display ultrasound images and/or various information processed by the ultrasound imaging apparatuses 1000a and 1000b. The main display 1210 and the sub-display 1220 may provide graphical user interfaces (GUI), thereby receiving user's inputs of data to control the ultrasound imaging apparatuses 1000a and 1000b. For example, the main display 1210 may display an ultrasound image and the sub-display 1220 may display a control panel to control display of the ultrasound image as a GUI. The sub-display 1220 may receive an input of data to control the display of an image through the control panel displayed as a GUI. The ultrasound imaging apparatuses 1000a and 1000b may control the display of the ultrasound image on the main display 1210 by using the input control data.

Referring to FIG. 11B, the ultrasound imaging apparatus 1000b may include a control panel 1650. The control panel 1650 may include buttons, trackballs, jog switches, or knobs, and may receive data to control the ultrasound imaging apparatus 1000b from the user. For example, the control panel 1650 may include a time gain compensation (TGC) button 1710 and a freeze button 1720. The TGC button 1710 is to set a TGC value for each depth of an ultrasound image. Also, when an input of the freeze button 1720 is detected during scanning an ultrasound image, the ultrasound imaging apparatus 1000b may keep displaying a frame image at that time point.

The buttons, trackballs, jog switches, and knobs included in the control panel 1650 may be provided as a GUI to the main display 1210 or the sub-display 1220.

Referring to FIG. 11C, the ultrasound imaging apparatus 1000c may include a portable device. An example of the portable ultrasound imaging apparatus 1000c may include, for example, smart phones including probes and applications, laptop computers, personal digital assistants (PDAs), or tablet PCs, but an exemplary embodiment is not limited thereto.

The ultrasound imaging apparatus 1000c may include the probe 20 and a main body 1400. The probe 20 may be connected to one side of the main body 1400 by wire or wirelessly. The main body 1400 may include a touch screen 1450. The touch screen 1450 may display an ultrasound image, various pieces of information processed by the ultrasound imaging apparatus 1000c, and a GUI.

The embodiments may be implemented as a software program including instructions stored in a computer-readable storage medium.

A computer may refer to a device configured to retrieve an instruction stored in the computer-readable storage medium and to operate, in response to the retrieved instruction, and may include an ultrasound imaging apparatus according to embodiments.

The computer-readable storage medium may be provided in the form of a non-transitory storage medium. In this regard, the term 'non-transitory' means that the storage medium does not include a signal and is tangible, and the term does not distinguish between data that is semi-permanently stored and data that is temporarily stored in the storage medium.

In addition, the ultrasound imaging apparatus or the method of controlling the ultrasound imaging apparatus according to embodiments may be provided in the form of a computer program product. The computer program product may be traded, as a product, between a seller and a buyer.

The computer program product may include a software program and a computer-readable storage medium having stored thereon the software program. For example, the computer program product may include a product (e.g. a downloadable application) in the form of a software program electronically distributed by a manufacturer of the ultrasound imaging apparatus or through an electronic market (e.g., Google™, Play Store™, and App Store™). For such electronic distribution, at least a part of the software program may be stored on the storage medium or may be temporarily generated. In this case, the storage medium may be a storage medium of a server of the manufacturer, a server of the electronic market, or a relay server for temporarily storing the software program.

In a system consisting of a server and a terminal (e.g., the ultrasound imaging apparatus), the computer program product may include a storage medium of the server or a storage medium of the terminal. Alternatively, in a case where a third device (e.g., a smartphone) that communicates with the server or the terminal is present, the computer program product may include a storage medium of the third device. Alternatively, the computer program product may include a software program that is transmitted from the server to the terminal or the third device or that is transmitted from the third device to the terminal.

In this case, one of the server, the terminal, and the third device may execute the computer program product, thereby performing the method according to embodiments. Alternatively, at least two of the server, the terminal, and the third device may execute the computer program product, thereby performing the method according to embodiments in a distributed manner.

For example, the server (e.g., a cloud server, an artificial intelligence (AI) server, or the like) may execute the computer program product stored in the server, and may control the terminal to perform the method according to embodiments, the terminal communicating with the server.

As another example, the third device may execute the computer program product, and may control the terminal to perform the method according to embodiments, the terminal communicating with the third device.

As another example, the third device may execute the computer program product, and may directly perform the method according to embodiments, based on at least one value input from an auxiliary device.

In a case where the third device executes the computer program product, the third device may download the computer program product from the server, and may execute the downloaded computer program product. Alternatively, the third device may execute the computer program product that is pre-loaded therein, and may perform the method according to the embodiments.

While embodiments of the present disclosure have been particularly shown and described with reference to the accompanying drawings, it will be understood by those of ordinary skill in the art that various changes in form and details may be made therein without departing from the spirit and scope of the invention as defined by the appended claims. The disclosed embodiments should be considered in descriptive sense only and not for purposes of limitation.

What is claimed is:

1. A method, performed by an ultrasound imaging apparatus, of registering a first image that is an ultrasound image and a second image that is an image from another modality, the method comprising:
    loading the second image pre-acquired for a patient;
    acquiring information about a position and an orientation of an ultrasound probe based on a three-dimensional positional relationship between at least one external electromagnetic sensor attached to a first feature point of a patient's body and an electromagnetic sensor of the ultrasound probe;

extracting, from the second image, a second feature point corresponding to the first feature point;

registering the first and second images based on the three-dimensional positional relationship between the at least one external electromagnetic sensor and the electromagnetic sensor of the ultrasound probe and on a position of the second feature point extracted from the second image; and displaying the first image in a first region of a display and the second image registered with the first image in a second region of the display, wherein the registering the first and second images comprises:

acquiring information about an angle between a first external electromagnetic sensor attached to the first feature point of the patient's body and a second external electromagnetic sensor attached to a structural feature point of the patient's body different from the first feature point; and correcting an angular error in the second image based on the information about the angle between the first external electromagnetic sensor and the second external electromagnetic sensor.

2. The method of claim 1, wherein the registering of the first and second images comprises:

setting, as a reference point, a position of the at least one external electromagnetic sensor attached to the first feature point; and matching a position and an angle of the second image to those of the first image based on information about a distance and an angle between the reference point and the electromagnetic sensor of the ultrasound probe.

3. The method of claim 1, wherein the extracting of the second feature point comprises extracting the second feature point including characteristics of a body structure corresponding to the first feature point by applying an image processing algorithm to the second image.

4. The method of claim 1, wherein the extracting of the second feature point comprises extracting the second feature point based on at least one of a specific part of an object in the second image, an anatomical structure of the object in the second image, a resolution of the second image, and characteristics of the second image.

5. The method of claim 1, wherein the extracting of the second feature point comprises extracting the second feature point from the second image by using a deep neural network (DNN) including at least one of a convolution neural network (CNN) and a recurrent neural network (RNN), or by using a machine learning model including a support vector machine (SVM).

6. The method of claim 1, wherein the extracting of the second feature point comprises:

receiving a user input for selecting, from the second image, a position of a structural feature point of the patient's body; and determining the position of the second feature point based on the received user input.

7. The method of claim 1, wherein the registering the first and second images comprises:

calculating a minimum distance between the second feature point extracted from the second image and a surface of the patient's body represented in the second image;

correcting the second feature point to a third feature point by moving the second feature point by the minimum distance; and registering the first image and the second image using the first feature point and the third feature point.

8. The method of claim 1, wherein the registering the first and second images comprises:

calculating a relationship of a distance and an angle between the second feature point extracted from the second image and a surface of the patient's body represented in the second image;

correcting the second feature point to a third feature point based on the calculated relationship of the distance and angle; and registering the first image and the second image using the first feature point and the third feature point.

9. The method of claim 1, wherein the displaying further comprising displaying, in the first image, a first marker indicating a position of the first feature point of the patient's body in the first image and displaying, in the second image, a second marker indicating the position of the second feature point extracted from the second image.

10. The method of claim 1, wherein the displaying further comprising displaying a graphical user interface (GUI) indicating a signal strength of each of the at least one external electromagnetic sensor.

11. An ultrasound imaging apparatus for registering a first image that is an ultrasound image and a second image that is an image from another modality, the ultrasound imaging apparatus comprising:

an ultrasound probe including an electromagnetic sensor;

a storage storing the second image pre-acquired for a patient, and the storage is a non-transitory computer-readable storage medium;

a memory storing at least one instruction for controlling an operation of the ultrasound imaging apparatus, and the memory is a non-transitory computer-readable storage medium;

a display; and a processor configured to execute the at least one instruction stored in the memory to:

load the second image from the storage;

acquire information about a position and an orientation of the ultrasound probe based on a three-dimensional positional relationship between at least one external electromagnetic sensor attached to a first feature point of a patient's body and the electromagnetic sensor of the ultrasound probe;

extract, from the second image, a second feature point corresponding to the first feature point;

register the first and second images based on the three-dimensional positional relationship between the at least one external electromagnetic sensor and the electromagnetic sensor of the ultrasound probe and on a position of the second feature point extracted from the second image; and display the first image in a first region of the display and the second image registered with the first image in a second region of the display, wherein the processor further configured to execute the at least one instruction to:

acquire information about an angle between a first external electromagnetic sensor attached to the first feature point of the patient's body and a second external electromagnetic sensor attached to a structural feature point of the patient's body different from the first feature point; and correct an angular error in the second image based on the information about the angle between the first external electromagnetic sensor and the second external electromagnetic sensor.

12. The ultrasound imaging apparatus of claim 11, wherein the processor is further configured to execute the at least one instruction to: set, as a reference point, a position of the at least one external electromagnetic sensor attached to the first feature point; and match a position and an angle of the second image to those of the first image based on information about a distance and an angle between the reference point and the electromagnetic sensor of the ultrasound probe.

13. The ultrasound imaging apparatus of claim 11, wherein the processor is further configured to execute the at least one instruction to extract the second feature point including characteristics of a body structure corresponding to the first feature point by applying an image processing algorithm to the second image.

14. The ultrasound imaging apparatus of claim 11, wherein the processor is further configured to execute the at least one instruction to extract the second feature point based on at least one of a specific part of an object in the second image, an anatomical structure of the object in the second image, a resolution of the second image, and characteristics of the second image.

15. The ultrasound imaging apparatus of claim 11, wherein the processor is further configured to execute the at least one instruction to extract the second feature point from the second image by using a deep neural network (DNN) including at least one of a convolution neural network (CNN) and a recurrent neural network (RNN), or by using a machine learning model including a support vector machine (SVM).

16. The ultrasound imaging apparatus of claim 11, further comprising a user input interface configured to receive a user input for selecting, from the second image, a position of a structural feature point of the patient's body,
wherein the processor is further configured to execute the at least one instruction to determine the position of the second feature point based on the received user input.

17. The ultrasound imaging apparatus of claim 11, wherein the processor is further configured to execute the at least one instruction to:
calculate a minimum distance between the second feature point extracted from the second image and a surface of the patient's body represented in the second image;
correct the second feature point to a third feature point by moving the second feature point by the minimum distance; and
register the first image and the second image using the first feature point and the third feature point.

18. The ultrasound imaging apparatus of claim 11, wherein
the processor is further configured to execute the at least one instruction to:
calculate a relationship of a distance and an angle between the second feature point extracted from the second image and a surface of the patient's body represented in the second image;
correct the second feature point to a third feature point based on the calculated relationship of the distance and angle; and
registering the first image and the second image using the first feature point and the third feature point.

19. The ultrasound imaging apparatus of claim 11, wherein the display further displays, in the first image, a first marker indicating a position of the first feature point of the patient's body in the first image and displays, in the second image, a second marker indicating the position of the second feature point extracted from the second image.

20. The ultrasound imaging apparatus of claim 11, wherein the display further displays a graphical user interface (GUI) indicating a signal strength of each of the at least one external electromagnetic sensor.

21. A computer program product comprising a non-transitory computer-readable storage medium, wherein the non-transitory computer-readable storage medium comprises instructions to:
load a second image pre-acquired for a patient;
acquire information about a position and an orientation of an ultrasound probe based on a three-dimensional positional relationship between at least one external electromagnetic sensor attached to a first feature point of a patient's body and an electromagnetic sensor of the ultrasound probe;
extract, from the second image, a second feature point corresponding to the first feature point;
register the first and second images based on the three-dimensional positional relationship between the at least one external electromagnetic sensor and the electromagnetic sensor of the ultrasound probe and on a position of the second feature point extracted from the second image; and
display the first image in a first region of a display and the second image registered with the first image in a second region of the display,
wherein the non-transitory computer-readable storage medium further comprises instructions to:
acquire information about an angle between a first external electromagnetic sensor attached to the first feature point of the patient's body and a second external electromagnetic sensor attached to a structural feature point of the patient's body different from the first feature point; and
correct an angular error in the second image based on the information about the angle between the first external electromagnetic sensor and the second external electromagnetic sensor.

\* \* \* \* \*